United States Patent
Lau et al.

[11] Patent Number: 6,066,167
[45] Date of Patent: May 23, 2000

[54] EXPANDABLE STENTS

[75] Inventors: Lilip Lau, Sunnyvale; William M. Hartigan, Fremont; John J. Frantzen, Copperopolis, all of Calif.

[73] Assignee: Advanced Cardiovascular Systems, Inc., Santa Clara, Calif.

[21] Appl. No.: 09/084,797

[22] Filed: May 26, 1998

Related U.S. Application Data

[62] Division of application No. 08/823,434, Mar. 24, 1997, Pat. No. 5,766,238, which is a division of application No. 08/783,097, Jan. 14, 1997, Pat. No. 5,735,893, which is a division of application No. 08/556,516, Nov. 13, 1995, Pat. No. 5,603,721, which is a division of application No. 08/281,790, Jul. 28, 1994, Pat. No. 5,514,154, which is a continuation-in-part of application No. 08/164,986, Dec. 9, 1993, abandoned, which is a continuation of application No. 07/783,558, Oct. 28, 1991, abandoned.

[51] Int. Cl.$^7$ ...................................................... A61F 2/00
[52] U.S. Cl. ............................................................... 623/1
[58] Field of Search ...................... 623/1, 12, 11

[56] References Cited

U.S. PATENT DOCUMENTS

| | | |
|---|---|---|
| 3,105,492 | 10/1963 | Jeckel . |
| 3,657,744 | 4/1972 | Ersek . |
| 3,993,078 | 11/1976 | Bergentz et al. . |
| 4,130,904 | 12/1978 | Whalen . |
| 4,140,126 | 2/1979 | Choudhury . |
| 4,159,719 | 7/1979 | Haerr . |
| 4,387,952 | 6/1983 | Slusher . |
| 4,503,569 | 3/1985 | Dotter . |
| 4,504,354 | 3/1985 | George et al. . |
| 4,512,338 | 4/1985 | Balko et al. . |
| 4,531,933 | 7/1985 | Norton et al. . |
| 4,553,545 | 11/1985 | Maass et al. . |
| 4,580,568 | 4/1986 | Gianturco . |
| 4,619,246 | 10/1986 | Molgaard-Nielsen et al. . |
| 4,649,922 | 3/1987 | Wiktor . |

(List continued on next page.)

FOREIGN PATENT DOCUMENTS

| | | |
|---|---|---|
| 0 221 570 A2 | 5/1987 | European Pat. Off. . |
| 0 380 668 | 10/1988 | European Pat. Off. . |
| 0 335 341 A1 | 10/1989 | European Pat. Off. . |
| 0 338 816 | 10/1989 | European Pat. Off. . |

(List continued on next page.)

OTHER PUBLICATIONS

Dotter, Charles T., Transluminally Placed Coilspring Endarterial Tube Grafts, *Investigative Radiology,* pp. 329–332, Sep./Oct. 1969.

Rösch, J., M.D., et al., Transjugular Intrahepatic Portacaval Shunt: An Experimental Work, *The American Journal of Surgery,* pp. 588–592, vol. 121, May 1971.

Dotter, Charles T., Transluminal Expandable Nitinol coil Stent Grafting: Preliminary Report, *Radiology Journal,* pp. 259–260, Apr. 1983.

Cragg, et al., Non–Surgical Placement of Arterial Endoprostheses: A New Technique Using Nitinol Wire, *Radiology Journal,* pp. 261–263, Apr. 1983.

Maass, et al., Radiological Follow–Up of Transluminally Inserted Vascular Endoprostheses: An Experimental Study Using Expanding Spirals, *Radiology Journal,* pp. 659–663, 1984.

(List continued on next page.)

*Primary Examiner*—Michael J. Milano
*Attorney, Agent, or Firm*—Fulwider Patton Lee & Utecht, LLP

[57] ABSTRACT

The invention is directed to an expandable stent for implantation in a body lumen, such as an artery, and a method for making it from a single length of tubing. The stent consists of a plurality of radially expandable cylindrical elements generally aligned on a common axis and interconnected by one or more interconnective elements. The individual radially expandable cylindrical elements consist of ribbon-like material disposed in an undulating pattern. Portions of the expanded stent project outwardly into engagement with the vessel wall to more securely attach the stent.

8 Claims, 4 Drawing Sheets

U.S. PATENT DOCUMENTS

| | | |
|---|---|---|
| 4,650,466 | 3/1987 | Luther . |
| 4,655,771 | 4/1987 | Wallsten . |
| 4,681,110 | 7/1987 | Wiktor . |
| 4,706,671 | 11/1987 | Weinrib . |
| 4,733,665 | 3/1988 | Palmaz . |
| 4,739,762 | 4/1988 | Palmaz . |
| 4,740,207 | 4/1988 | Kreamer . |
| 4,762,128 | 8/1988 | Rosenbluth . |
| 4,767,418 | 8/1988 | Deininger . |
| 4,776,337 | 10/1988 | Palmaz . |
| 4,795,458 | 1/1989 | Regan . |
| 4,800,882 | 1/1989 | Gianturco . |
| 4,830,003 | 5/1989 | Wolff et al. . |
| 4,848,343 | 7/1989 | Wallsten et al. . |
| 4,856,516 | 8/1989 | Hillstead . |
| 4,870,966 | 10/1989 | Dellon et al. . |
| 4,877,030 | 10/1989 | Beck et al. . |
| 4,878,906 | 11/1989 | Lindemann et al. . |
| 4,886,062 | 12/1989 | Wiktor . |
| 4,892,539 | 1/1990 | Koch . |
| 4,893,623 | 1/1990 | Rosenbluth . |
| 4,907,336 | 3/1990 | Gianturco . |
| 4,913,141 | 4/1990 | Hillstead . |
| 4,922,905 | 5/1990 | Strecker . |
| 4,943,346 | 7/1998 | Mattelin . |
| 4,950,227 | 8/1990 | Savin et al. . |
| 4,963,022 | 10/1990 | Sommargren . |
| 4,969,458 | 11/1990 | Wiktor . |
| 4,969,890 | 11/1990 | Sugita et al. . |
| 4,986,831 | 1/1991 | King et al. . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold et al. . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Gianturco et al. . |
| 5,037,377 | 8/1991 | Alonso . |
| 5,037,392 | 8/1991 | Hillstead . |
| 5,037,427 | 8/1991 | Harada et al. . |
| 5,041,126 | 8/1991 | Gianturco . |
| 5,059,211 | 10/1991 | Stack et al. . |
| 5,061,275 | 10/1991 | Wallsten et al. . |
| 5,062,829 | 11/1991 | Pryor et al. . |
| 5,064,435 | 11/1991 | Porter . |
| 5,071,407 | 12/1991 | Termin et al. . |
| 5,073,694 | 12/1991 | Tessier et al. . |
| 5,078,720 | 1/1992 | Burton et al. . |
| 5,078,726 | 1/1992 | Kreamer . |
| 5,078,736 | 1/1992 | Behl . |
| 5,084,065 | 1/1992 | Weldon et al. . |
| 5,089,005 | 2/1992 | Harada . |
| 5,089,006 | 2/1992 | Stiles . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,108,416 | 4/1992 | Ryan et al. . |
| 5,108,417 | 4/1992 | Sawyer . |
| 5,116,318 | 5/1992 | Hillstead . |
| 5,116,360 | 5/1992 | Pinchuk et al. . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,536 | 8/1992 | Hillstead . |
| 5,158,548 | 10/1992 | Lau et al. . |
| 5,161,547 | 11/1992 | Tower . |
| 5,163,958 | 11/1992 | Pinchuk . |
| 5,171,262 | 12/1992 | MacGregor . |
| 5,180,368 | 1/1993 | Garrison . |
| 5,183,085 | 2/1993 | Timmermans . |
| 5,192,297 | 3/1993 | Hull . |
| 5,192,307 | 3/1993 | Wall . |
| 5,195,984 | 3/1993 | Schatz . |
| 5,197,978 | 3/1993 | Hess . |
| 5,222,971 | 6/1993 | Willard et al. . |
| 5,226,913 | 7/1993 | Pinchuk . |
| 5,234,456 | 8/1993 | Silvestrini . |
| 5,242,452 | 9/1993 | Inoue . |
| 5,282,823 | 2/1994 | Schwartz et al. . |
| 5,282,824 | 2/1994 | Gianturco . |
| 5,290,305 | 3/1994 | Inoue . |
| 5,292,331 | 3/1994 | Boneau . |
| 5,304,200 | 4/1994 | Spaulding . |
| 5,314,444 | 5/1994 | Gianturco . |
| 5,314,472 | 5/1994 | Fontaine . |
| 5,330,500 | 7/1994 | Song . |
| 5,356,433 | 10/1994 | Rowland et al. . |
| 5,423,885 | 6/1995 | Williams . |
| 5,449,373 | 9/1995 | Pinchasik ................................. 623/1 |
| 5,716,396 | 2/1998 | Williams ................................. 623/1 |
| 5,733,303 | 3/1998 | Israel ........................................ 623/1 |
| 5,733,325 | 3/1998 | Robinson ................................ 623/1 |
| 5,800,521 | 9/1998 | Orth .......................................... 623/1 |
| 5,817,152 | 10/1998 | Birdsall ..................................... 623/1 |

FOREIGN PATENT DOCUMENTS

| | | |
|---|---|---|
| 0 357 003 A2 | 3/1990 | European Pat. Off. . |
| 0 361 192 | 4/1990 | European Pat. Off. . |
| 0 364 787 A1 | 4/1990 | European Pat. Off. . |
| 0 372 789 A3 | 6/1990 | European Pat. Off. . |
| 0 407 951 | 1/1991 | European Pat. Off. . |
| 0 421 729 A2 | 4/1991 | European Pat. Off. . |
| 0 423 916 A1 | 4/1991 | European Pat. Off. . |
| 0 428 479 A1 | 5/1991 | European Pat. Off. . |
| 0 517 075 A1 | 5/1992 | European Pat. Off. . |
| 0 062 300 | 10/1992 | European Pat. Off. . |
| 0 540 290 A2 | 10/1992 | European Pat. Off. . |
| 0 517 075 | 12/1992 | European Pat. Off. . |
| 0 540290 A2 | 5/1993 | European Pat. Off. . |
| 0 541 443 A1 | 5/1993 | European Pat. Off. . |
| 2 677872 | 12/1992 | France . |
| 58-501458 | 9/1983 | Japan . |
| 62-231657 | 10/1987 | Japan . |
| 62-235496 | 10/1987 | Japan . |
| 63-21464 | 9/1988 | Japan . |
| 64-83685 | 3/1989 | Japan . |
| 1-299550 | 12/1989 | Japan . |
| 2-174859 | 7/1990 | Japan . |
| 2-255157 | 10/1990 | Japan . |
| 3-9745 | 1/1991 | Japan . |
| 3-9746 | 1/1991 | Japan . |
| 3-151983 | 6/1991 | Japan . |
| 425755 | 2/1992 | Japan . |
| 2 070 490 | 9/1981 | United Kingdom . |
| 2 135 585 | 9/1984 | United Kingdom . |
| WO 91/07139 | 5/1991 | WIPO . |
| WO 92/06734 | 4/1992 | WIPO . |
| WO 92/09246 | 6/1992 | WIPO . |

OTHER PUBLICATIONS

70th Scientific Assembly and Annual Meeting: Scientific Program, *Radiology*, Washington, D.C., Nov. 25–30, 1984, special Edition, vol. 153(P).

C.R. Bard, PE Plus Peripheral Balloon Dilation Catheter, *C.R. Bard, Inc.,* Aug. 1985.

Wright, et al., Percutaneous Endovascular Stents: an Experimental Evaluation, *Radiology Journal,* pp. 69–72, 1985.

Charnsangavej, C., M.D., et al., Endovascular Stent for Use in aortic Dissection: An In Vitro Experiment, *radiology,* pp. 323–324, vol. 157, No. 2, Nov. 1985.

Palmaz, et al., Expandable Intraluminal Graft: A Preliminary Study, *Radiology Journal,* pp. 73–77, 1985.

72nd Scientific Assembly and Annual Meeting: RSNA Scientific Progam, *Radiology,* Chicago: Nov. 30–Dec. 5, 1986, Special Edition, vol. 161(P).

Wallace, Michael J., et al., Tracheobronchial Tree: Expandable Metallic Stents Used in Experimental and Clinical Applications (Work in Progress), *Radiology,* pp. 309–312, vol. 158, Feb. 1986.

Charnsangavej, Chuslip, M.D., et al., Stenosis of the Venaq Cava: Preliminary Assessment of Treatment With Expandable Metallic Stents, *Radiology,* pp. 295–298, vo.. 161, Nov. 1986.

Duprat, et al., Flexible Balloon–Expanded Stent for Small Vessels, *Radiology Journal,* pp. 276–278, 1987.

Rösch, Josef, M.D., et al., Experimental Intrahepatic Portacaval Anastomosis: Use of Expandable Gianturco Stents, *Radiology,* pp. 481–485, vol. 162, Feb. 1987.

Rösch, Josef, M.D., et al., Gianturco Expandable Stents in Experimental and Clinical Use, paper presented at The Twelth Annual Course on "Diagnostic Angiography and Interventional Radiology" Mar. 23–26, 1987 (Pittsburgh, Pennsylvania).

Lawrence, David D., Jr., M.D., et al., Percutaneous Endovascular Graft: Experimental Evaluation, *Radiology,* pp. 357–360, vol. 163, May 1987.

Rösch, Josef, M.D., et al., Gianturco Expandable Wire Stents in the Treatment of Superior Vena Cava Syndrome Recurring After Maximum–Tolerance Radiation, *Cancer,* pp. 1243–1246, vol. 60, Sep. 1987.

Yoshioka, Tetsuya, et al., Self–Expanding Endovascular Graft: An Experimental Study in Dogs, *American Journal of Roentgeriology,* pp. 673–676, vol. 151, Oct. 1988.

Rösch, Josef, M.D., et al., Modified Gianturco Expandable Wire Stents in Experimental and Clinical Use, *Annales de Radiologie,* pp. 100–103, vol. 31, No. 2, 1988.

Anomnatic™ II Positioning Controller, Anorad Corporation, Brochure.

Program: Day 2 (Nov. 18) The Radiological Society of North America, *Radiology,* Chicago: Nov. 30–Dec. 5, 1986, Special Edition, vol. 161(P).

Mirich, David et al. "Percutaneously Placed Endovascular Grafts for Aoertic Aneurysms: Feasibility Study," *Radiology,* 1989, part 2, p1033–37.

Yoshioka, Tetsuya et al. "Development and Clinical Application of Biliary Endoprosthesis Using Expandable Metallic Stents," *Japan Radiological Society,* 1988, vol. 48, No. 9, pp. 1183–1185. (with translation).

Yoshioka, et al. "Self Expanding Endovascular Graft: An Experimental Study in Dogs," *American Journal of Roentgeriology,* 1988, vol. 151, pp. 673–676.

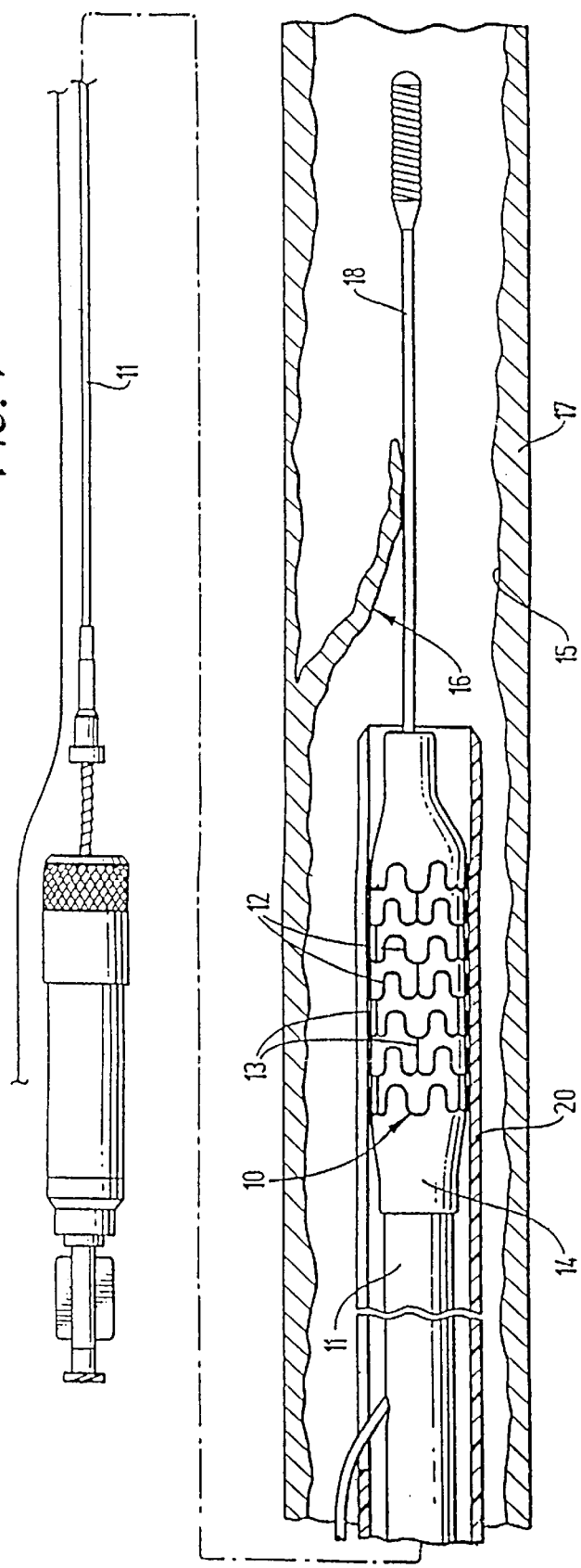
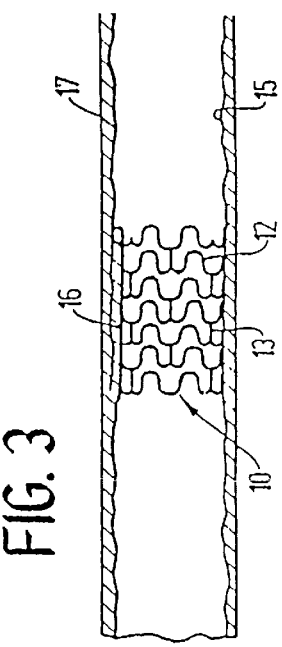
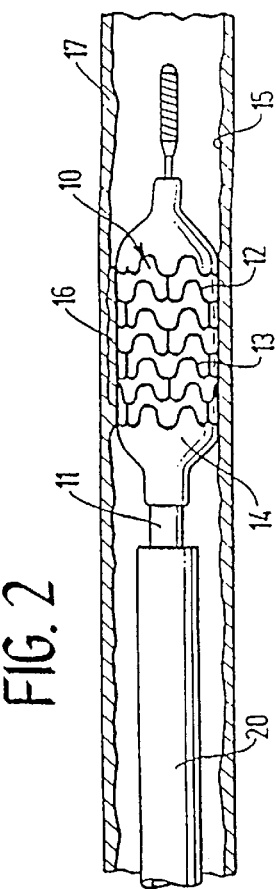

EXPANDABLE STENTS

RELATED APPLICATIONS

This application is a division of U.S. Ser. No. 08/823,434, filed Mar. 24, 1997, now U.S. Pat. No. 5,766,238, which is a division of U.S. Ser. No. 08/783,097, filed Jan. 14, 1997, now U.S. Pat. No. 5,735,893, which is a division of U.S. Ser. No. 08/556,516, filed Nov. 13, 1995, now U.S. Pat. No. 5,603,721, which is a division of U.S. Ser. No. 08/281,790, filed Jul. 28, 1994, now U.S. Pat. No. 5,514,154, which is a continuation-in-part of U.S. patent application Ser. No. 08/164,986 filed Dec. 9, 1993, now abandoned, which is a continuation application of U.S. Ser. No. 07/783,558 filed Oct. 28, 1991, now abandoned.

BACKGROUND OF INVENTION

This invention relates to expandable endoprosthesis devices, generally called stents, which are adapted to be implanted into a patient's body lumen, such as blood vessel, to maintain the patency thereof. These devices are very useful in the treatment of atherosclerotic stenosis in blood vessels.

Stents are generally tubular-shaped devices which function to hold open a segment of a blood vessel or other anatomical lumen. They are particularly suitable for use to support and hold back a dissected arterial lining which can occlude the fluid passageway therethrough.

Further details of prior art stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); and U.S. Pat. No. 4,886,062 (Wiktor), which are hereby incorporated herein in their entirety by reference thereto.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery.

What has been needed and heretofore unavailable is a stent which has a high degree of flexibility so that it can be advanced through tortuous passageways and can be readily expanded and yet have the mechanical strength to hold open the body lumen into which it expanded. The present invention satisfies this need.

SUMMARY OF THE INVENTION

The present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein.

The stent of the invention generally includes a plurality of radially expandable cylindrical elements which are relatively independent in their ability to expand and to flex relative to one another. The individual radially expandable cylindrical elements of the stent are dimensioned so as to be longitudinally shorter than their own diameters. Interconnecting elements or struts extending between adjacent cylindrical elements provide increased stability and a preferable position to prevent warping of the stent upon the expansion thereof. The resulting stent structure is a series of radially expandable cylindrical elements which are spaced longitudinally close enough so that small dissections in the wall of a body lumen may be pressed back into position against the lumenal wall, but not so close as to compromise the longitudinal flexibilities of the stent. The individual cylindrical elements may rotate slightly relative to adjacent cylindrical elements without significant deformation, cumulatively giving a stent which is flexible along its length and about its longitudinal axis but is still very stiff in the radial direction in order to resist collapse.

The stent embodying features of the invention can be readily delivered to the desired lumenal location by mounting it on an expandable member of a delivery catheter, for example a balloon, and passing the catheter-stent assembly through the body lumen to the implantation site. A variety of means for securing the stent to the expandable member on the catheter for delivery to the desired location are available. It is presently preferred to compress the stent onto the balloon. Other means to secure the stent to the balloon include providing ridges or collars on the inflatable member to restrain lateral movement, or using bioresorbable temporary adhesives.

The presently preferred structure for the expandable cylindrical elements which form the stents of the present invention generally circumferential undulating pattern, e.g. serpentine. The transverse cross-section of the undulating component of the cylindrical element is relatively small and preferably has an apect ratio of about two to one to about 0.5 to one. A one to one apect ratio has been found particularly suitable. The open reticulated structure of the stent allows for the perfusion of blood over a large portion of the arterial wall which can improve the healing and repair of a damaged arterial lining.

The radial expansion of the expandable cylinder deforms the undulating pattern thereof similar to changes in a waveform which result from decreasing the waveform's amplitude and the frequency. Preferably, the undulating patterns of the individual cylindrical structures are in phase with each other in order to prevent the contraction of the stent along its length when it is expanded. The cylindrical structures of the stent are plastically deformed when expanded (except with NiTi alloys) so that the stent will remain in the expanded condition and therefore they must be sufficiently rigid when expanded to prevent the collapse thereof in use. During expansion of the stent, portions of the undulating pattern will tip outwardly resulting in projecting members on the outer surface of the expanded stent. These projecting members tip radially outwardly from the outer surface of the stent and embed in the vessel wall and help secure the expanded stent so that it does not move once it is implanted.

With superelastic NiTi alloys, the expansion occurs when the stress of compression is removed so as to allow the phase transformation from austenite back to martensite and as a result the expansion of the stent.

The elongated elements which interconnect adjacent cylindrical elements should have a transverse cross-section similar to the transverse dimensions of the undulating components of the expandable cylindrical elements. The interconnecting elements may be formed in a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. Preferably, all of the interconnecting elements of a stent are joined at either the peaks or the valleys of the undulating structure of the cylindrical elements which for the stent. In this manner there is no shortening of the stent upon expansion.

The number and location of elements interconnecting adjacent cylindrical elements can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In a presently preferred embodiment of the invention the stent is conveniently and easily formed by coating stainless steel tubing with a material resistant to chemical etching, removing portions of the coating to expose portions of underlying tubing which are to be removed to develop the desired stent structure. The exposed portions of the tubing are removed by chemically etching from the tubing exterior leaving the coated portion of the tubing material in the desired pattern of the stent structure. The etching process develops smooth openings in the tubing wall without burrs or other artifacts which are characteristic of mechanical or laser machining processes in the small sized products contemplated. Moreover, a computer controlled laser patterning process to remove the chemical resistive coating makes photolithography technology adaptable to the manufacture of these small products. The forming of a mask in the extremely small sizes needed to make the small stents of the invention would be a most difficult task. A plurality of stents can be formed from one length of tubing by repeating the stent pattern and providing small webs or tabs to interconnect the stents. After the etching process, the stents can be separated by severing the small webs or tabs which connect them.

Other features and advantages of the present invention will become more apparent from the following detailed description of the invention. When taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery, pressing the damaged lining against the arterial wall.

FIG. 3 is an elevational view, partially in section showing the expanded stent within the artery after withdrawal of the delivery catheter.

DETAILED DESCRIPTION OF THE PREFERRED EMBODIMENTS

Figures 4, 5, 6:
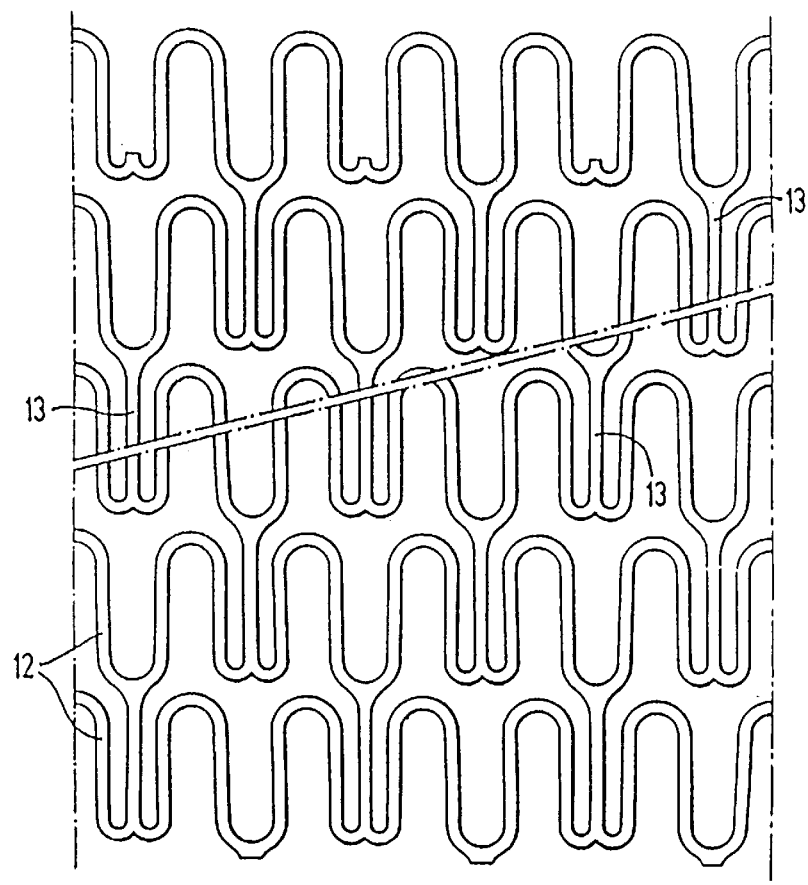
FIG. 4 is a perspective view of a stent embodying features of the invention in an unexpanded state, with one end of the stent being shown in an exploded view illustrate the details thereof.
FIG. 5 is a plan view of a flattened section of a stent of the invention which illustrates the undulating pattern of the stent shown in FIG. 4.
FIG. 6 is a schematic representation of equipment for selectively removing coating applied to tubing in the manufacturing of the stents of the present invention.
Figure 7:
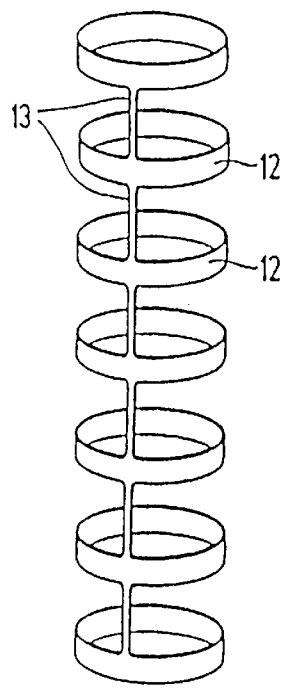
FIGS. 7 through 10 are perspective views schematically illustrating various configurations of interconnective element placement between the radially expandable cylindrical elements of the stent.
Figure 8:
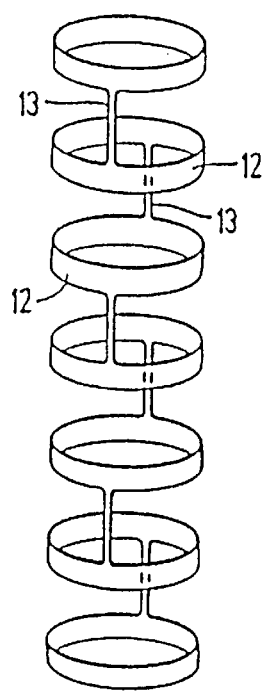
Figure 9:
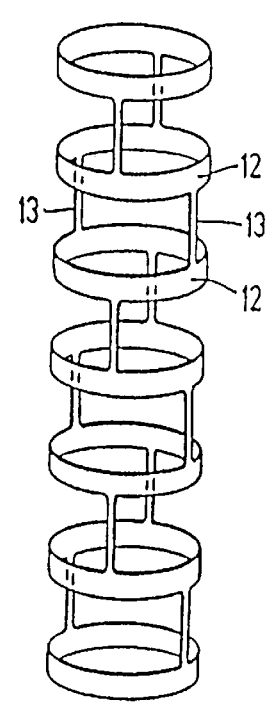

FIG. 1 illustrates a stent 10 incorporating features of the invention which is mounted onto a delivery catheter 11. The stent generally comprises a plurality of radially expandable cylindrical elements 12 disposed generally coaxially and interconnected by elements 13 disposed between adjacent cylindrical elements. The delivery catheter 11 has an expandable portion or balloon 14 for expanding of the stent 10 within an artery 15. The artery 15, as shown in FIG. 1 has a dissected lining 16 which has occluded a portion of the arterial passageway.

The delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is compressed onto the balloon. A retractable protective delivery sleeve 20 as described in co-pending applications Ser. No. 07/647,464 filed on Apr. 25, 1990 and entitled STENT DELIVERY SYSTEM may be provided to further ensure that the stent stays in place on the expandable portion of the delivery catheter 11 and prevent abrasion of the body lumen by the open surface of the stent 20 during delivery to the desired arterial location. Other means for securing the stent 10 onto the balloon 14 may also be used, such as providing collars or ridges on the ends of the working portion, i.e. the cylindrical portion, of the balloon.

Each radially expandable cylindrical element 12 of the stent 10 may be independently expanded. Therefore, the balloon 14 may be provided with an inflated shape other than cylindrical, e.g. tapered, to facilitate implantation of the stent 10 in a variety of body lumen shapes.

In a preferred embodiment, the delivery of the stent 10 is accomplished in the following manner. The stent 10 is first mounted onto the inflatable balloon 14 on the distal extremity of the delivery catheter 11. The balloon 14 is slightly inflated to secure the stent 10 onto the exterior of the balloon. The catheter-stent assembly is introduced within the patient's vasculature in a conventional Seldinger technique through a guiding catheter (not shown). A guidewire 18 is disposed across the damaged arterial section with the detached or dissected lining 16 and then the catheter-stent assembly is advanced over a guidewire 18 within the artery 15 until the stent 10 is directly under the detached lining 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent 10 from elongated tubular member, the undulating component of the cylindrical elements of the stent 10 is relatively flat in transverse cross-section, so that when the stent is expanded, the cylindrical elements are pressed into the wall of the artery 15 and as a result do not interfere with the blood flow through the artery 15. The cylindrical elements 12 of stent 10 which are pressed into the wall of the artery 15 will eventually be covered with endothelial cell growth which further minimizes blood flow interference. The undulating portion of the cylindrical sections 12 provide good tacking characteristics to prevent stent movement within the artery. Furthermore, the closely spaced cylindrical elements 12 at regular intervals provide uniform support for the wall of the artery 15, and consequently are well adapted to tack up and hold in place small flaps or dissections in the wall of the artery 15 as illustrated in FIGS. 2 and 3.

FIG. 4 is an enlarged perspective view of the stent 10 shown in FIG. 1 with one end of the stent shown in an exploded view to illustrate in greater detail the placement of interconnecting elements 13 between adjacent radially expandable cylindrical elements 12. Each pair of the interconnecting elements 13 on one side of a cylindrical element 12 are preferably placed to achieve maximum flexibility for a stent. In the embodiment shown in FIG. 4 the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible, and several examples are illustrated schematically in FIGS. 7–10. However, as previously mentioned, all of the interconnecting elements of an individual stent should be secured to either the peaks or valleys of the undulating structural elements in order to prevent shortening of the stent during the expansion thereof.

Figure 10:
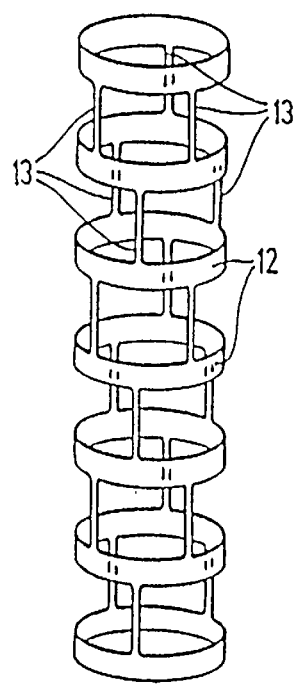

FIG. 10 illustrates a stent of the present invention wherein three interconnecting elements 12 are disposed between radially expandable cylindrical elements 11. The interconnecting elements 12 are distributed radially around the circumference of the stent at a 120-degree spacing. Disposing four or more interconnecting elements 13 between adjacent cylindrical elements 12 will generally give rise to the same considerations discussed above for two and three interconnecting elements.

Figure 11:
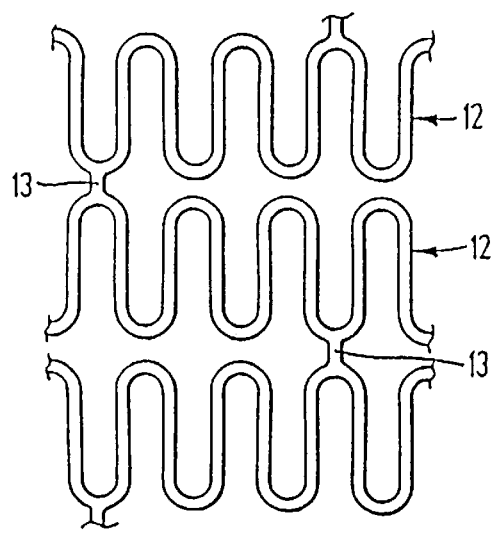
FIG. 11 is a plan view of a flattened section of a stent illustrating an alternate undulating pattern in the expandable cylindrical elements of the stent which are out of phase.
Figure 12:
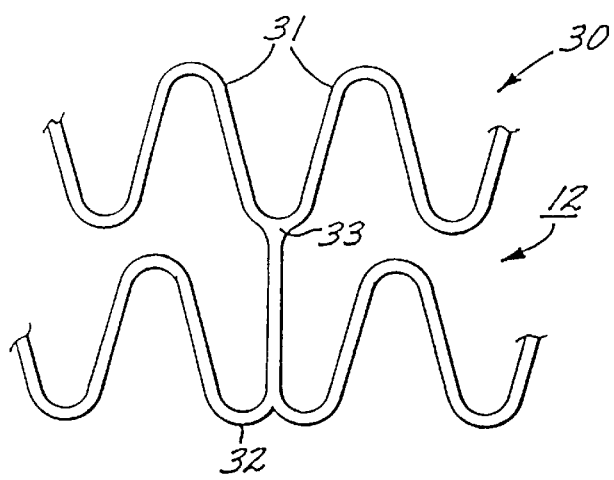
FIG. 12 is an enlarged partial view of the stent of FIG. 5 with the various members slightly expanded.

The properties of the stent 10 may also be varied by alteration of the undulating pattern of the cylindrical elements 13. FIG. 11 illustrates an alternative stent structure in which the cylindrical elements are in serpentine patterns but out of phase with adjacent cylindrical elements. The particular pattern and how many undulations per unit of length around the circumference of the cylindrical element 13, or the amplitude of the undulations, are chosen to fill particular mechanical requirements for the stent such as radial stiffness.

The number of undulations may also be varied to accommodate placement of interconnecting elements 13, e.g. at the peaks of the undulations or along the sides of the undulations as shown in FIGS. 5 and 11.

In keeping with the invention, and with reference to FIGS. 4 and 12–14, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32, and Y-shaped members 33, each having a different radius so that expansion forces are more evenly distributed over the various members.

Figure 13:
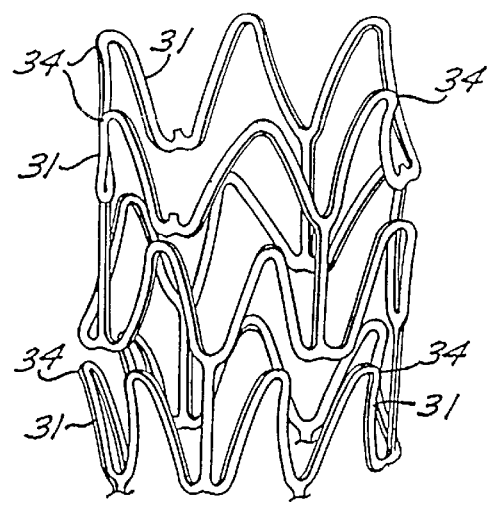
FIG. 13 is a perspective view of the stent of FIG. 4 after it is fully expanded depicting some members projecting radially outwardly.
Figure 14:
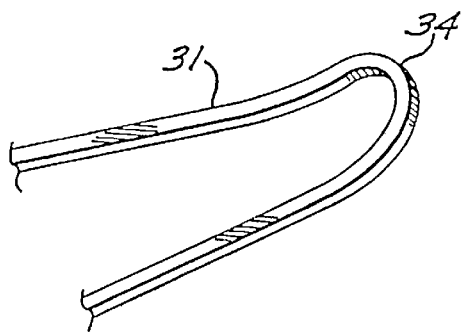
FIG. 14 is an enlarged, partial perspective view of one U-shaped member with its tip projecting outwardly after expansion.

As depicted in FIGS. 13 and 14, after cylindrical elements 12 have been radially expanded, outwardly projecting edges 34 are formed. That is, during radial expansion U-shaped members 31 will tip outwardly thereby forming outwardly projecting edges. These outwardly projecting edges provide for a roughened outer wall surface of stent 10 and assist in implanting the stent in the vascular wall by embedding into the vascular wall. In other words, outwardly projecting edges embed into the vascular wall, for example artery 15, as depicted in FIG. 3. Depending upon the dimensions of stent 10 and the thickness of the various members making up the serpentine pattern 30, any of the U-shaped members 31, W-shaped members 32, and Y-shaped members 33 can tip radially outwardly to form a projecting edge 34. It is most likely and preferred that U-shaped members 31 tip outwardly since they do not join with any connecting member 13 to prevent them from expanding outwardly.

The stent 10 of the present invention can be made in many ways. However, the preferred method of making the stent is to coat a thin-walled tubular member, such as stainless steel tubing, with a material which is resistive to chemical etchants, remove portions of the coating to expose underlying tubing which is to be removed but to leave coated portions of the tubing in the desired pattern for the stent so that subsequent etching will remove the exposed portions of the metallic tubing, but will leave relatively untouched the portions of the metallic tubing which are to form the stent. The coated portion of the metallic tube is in the desired shape for the stent. An etching process avoids the necessity of removing burrs or slag inherent in conventional or laser machining process. It is preferred to remove the etchant-resistive material by means of a machine-controlled laser as illustrated schematically in FIG. 6.

A coating is applied to a length of tubing which, when cured, is resistive to chemical etchants. "Blue Photoresist" made by the Shipley Company in San Jose, Calif., is an example of suitable commercially available photolithographic coatings. The coating is preferably applied by electrophoretic deposition.

To ensure that the surface finish is reasonably uniform, one of the electrodes used for the electrochemical polishing is a doughnut-shaped electrode which is placed about the central portion of the tubular member.

The tubing may be made of suitable biocompatible material such as stainless steel, titanium, tantalum, superelastic NiTi alloys and even high strength thermoplastic polymers. The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch. In the instance when the stent was plastic, it would have to be heated within the arterial site where the stent is expanded to facilitate the expansion of the stent. Once expanded, it would then be cooled to retain its expanded state. The stent may be conveniently heated by heating the fluid within the balloon or the balloon directly by a suitable system such as disclosed in a co-pending application Ser. No. 07/521,337, filed Jan. 26, 1990 entitled DILATATION CATHETER ASSEMBLY WITH HEATED BALLOON which is incorporated herein in its entirety by reference. The stent may also be made of materials such as superelastic NiTi alloys such as described in co-pending application Ser. No. 07/629,381, filed Dec. 18, 1990, entitled SUPERELASTIC GUIDING MEMBER which is incorporated herein in its entirety by reference. In this case the stent would be formed full size but deformed (e.g. compressed) into a smaller diameter onto the balloon of the delivery catheter to facilitate transfer to a desired intraluminal site. The stress induced by the deformation transforms the stent from a martensite phase to an austenite phase and upon release of the force, when the stent reaches the desired intraluminal location, allows the stent to expand due to the transformation back to the martensite phase.

Referring to FIG. 6, the coated tubing 21 is put in a rotatable collet fixture 22 of a machine controlled apparatus 23 for positioning the tubing 21 relative to a laser 24. According to machine-encoded instructions, the tubing 21 is rotated and moved longitudinally relative to the laser 24 which is also machine controlled. The laser selectively removes the etchant-resistive coating on the tubing by ablation and a pattern is formed such that the surface of the tube that is to be removed by a subsequent chemical etching process is exposed. The surface of the tube is therefore left coated in the discrete pattern of the finished stent.

A presently preferred system for removing the coating on the tubing includes the use an 80-watt $CO_2$ laser, such as a Coherent Model 44, in pulse mode (0.3 mS pulse length); 48 mA key current and 48 W key power with 0.75 W average power, at 100 Hz; Anorad FR=20; 12.5 Torr; with no assist gas. Low pressure air is directed through the fine focus head to ensure that no vapor contacts the lens. The assist gas jet assembly on the laser unit may be removed to allow a closer proximity of the fine focus head and the collet fixture. Optimum focus is set at the surface of the tubing. Cured photo-resist coating readily absorbs the energy of the $CO_2$ wavelength, so that it can be readily removed by the laser. A coated 4-inch length of 0.06 inch stainless steel tubing is preferred and four stents can be patterned on the length of tubing. Three tabs or webs between stents provide good handling characteristics for the tubing after the etching process.

The process of patterning the resistive coating on the stent is automated except for loading and unloading the length of tubing. Referring again to FIG. 6 it may be done, for example, using a CNC-opposing collet fixture 22 for axial rotation of the length of tubing, in conjunction with a CNC X/Y table 25 to move the length of tubing axially relative to a machine-controlled laser as described. The entire space between collets can be patterned using the $CO_2$ laser set-up of the foregoing example. The program for control of the apparatus is dependent on the particular configuration used and the pattern to be ablated in the coating, but is otherwise conventional.

This process makes possible the application of present photolithography technology in manufacturing the stents. While there is presently no practical way to mask and expose a tubular photo-resist coated part of the small size required for making intravascular stents, the foregoing steps eliminate the need for conventional masking techniques.

After the coating is thus selectively ablated, the tubing is removed from the collet fixture 22. Next, wax such at ThermoCote N-4 is heated to preferably just above its melting point, and inserted into the tubing under vacuum or pressure. After the wax has solidified upon cooling, it is reheated below its melting point to allow softening, and a smaller diameter stainless steel shaft is inserted into the softened wax to provide support. The tubing is then etched chemically in a conventional manner. After cutting the tabs connecting the stents any surface roughness or debris from the tabs is removed. The stents are preferably electrochemically polished in an acidic aqueous solution such as a solution of ELECTRO-GLO #300, sold by the ELECTRO-GLO CO., Inc. in Chicago, Ill., which is a mixture of sulfuric acid, carboxylic acids, phosphates, corrosion inhibitors and a biodegradable surface active agent. The bath temperature is maintained at about 110–135 degrees F. and the current density is about 0.4 to about 1.5 amps per in.$^2$ Cathode to anode area should be at least about two to one. The stents may be further treated if desired, for example by applying a biocompatible coating.

While the invention has been illustrated and described herein in terms of its use as an intravascular stent, it will be apparent to those skilled in the art that the stent can be used in other instances such as to expand prostatic urethras in cases of prostate hyperplasia. Other modifications and improvements may be made without departing from the scope of the invention.

Other modifications and improvements can be made to the invention without departing from the scope thereof.

What is claimed is:

1. A longitudinally flexible stent for implanting in a body lumen, comprising;
    a first cylindrically shaped element, a second cylindrically shaped element, a third cylindrically shaped element, up to an Nth cylindrically shaped element, the cylindrically shaped elements being generally independently expandable in the radial direction and generally aligned on a common longitudinal axis;
    other than the first and the Nth cylindrically shaped elements, each of the cylindrically shaped elements has two adjacent cylindrically shaped elements spaced in opposite axial directions;
    each of the cylindrically shaped elements having an undulating pattern of peaks and valleys, the undulating pattern of each of the cylindrically shape elements being out of phase with the undulating pattern of each of the adjacent cylindrically shaped elements; and
    each of the cylindrically shaped elements being interconnected to one of the adjacent cylindrically shaped elements so that the cylindrically shaped elements form a longitudinally flexible stent.

2. The stent of claim 1, wherein the distance between adjacent cylindrically shaped elements is less than the width of either a single peak or a single valley.

3. The stent of claim 1, wherein each of the cylindrically shaped elements includes at least three peaks and three valleys.

4. The stent of claim 1, wherein the peaks and valleys have a substantially U-shaped configuration.

5. A longitudinally flexible stent for implanting in a body lumen, comprising;

a first cylindrically shaped element, a second cylindrically shaped element, a third cylindrically shaped element, up to an Nth cylindrically shaped element, the cylindrically shaped elements being generally independently expandable in the radial direction and generally aligned on a common longitudinal axis;

each of the cylindrically shaped elements having an undulating pattern of peaks and valleys, the undulating pattern of each of the cylindrically shaped elements being out of phase with the undulating pattern of each of the adjacent cylindrically shaped elements; and each of the cylindrically shaped elements being interconnected to one of the adjacent cylindrically shaped elements so that the cylindrically shaped elements form a longitudinally flexible stent.

6. The stent of claim 5, wherein the distance between adjacent cylindrically shaped elements is less than the width of either a single peak or a single valley.

7. The stent of claim 5, wherein each of the cylindrically shaped elements includes at least three peaks and three valleys.

8. The stent of claim 5, wherein the peaks and valleys have a substantially U-shaped configuration.

* * * * *

UNITED STATES PATENT AND TRADEMARK OFFICE
CERTIFICATE OF CORRECTION

PATENT NO. : 6,066,167
DATED : May 23, 2000
INVENTOR(S) : Lilip Lau, William M. Hartigan, John J. Frantzen It is certified that error appears in the above-identified patent and that said Letters Patent is hereby corrected as shown below:

Column 4, line 50, change "20", to read --10--.

Column 5, lines 56 & 58, change "12", to read --13--, two places.

Column 6, line 3, change "13", to read --12--.

Signed and Sealed this

Twenty-seventh Day of March, 2001

*Attest:*

NICHOLAS P. GODICI

*Attesting Officer*   Acting Director of the United States Patent and Trademark Office

Disclaimer 6,066,167—Lilip Lau, Sunnyvale; William M. Hartigan, Fremont; John J. Frantzen, Copperopolis, all of Calif. EXPANDABLE STENTS. Patent dated May 23, 2000. Disclaimer filed May 31, 2002 by the assignee, Advanced Cardiovascular Systems Inc.

The term of this patent shall not extend beyond the expiration date of Pat. No. 5,514,154
*(Official Gazette, August 13, 2002)*

(12) EX PARTE REEXAMINATION CERTIFICATE (7496th)
United States Patent
Lau et al.

(10) Number: US 6,066,167 C1
(45) Certificate Issued: May 11, 2010

(54) EXPANDABLE STENTS

(75) Inventors: Lilip Lau, Sunnyvale, CA (US); William M. Hartigan, Fremont, CA (US); John J. Frantzen, Copperopolis, CA (US)

(73) Assignee: Advanced Cardiovascular Systems, Inc., Santa Clara, CA (US)

Reexamination Request:
No. 90/007,889, Jan. 23, 2006
No. 90/008,620, May 7, 2007
No. 90/009,159, May 23, 2008

Reexamination Certificate for:
Patent No.: 6,066,167
Issued: May 23, 2000
Appl. No.: 09/084,797
Filed: May 26, 1998

Certificate of Correction issued Mar. 27, 2001.

Related U.S. Application Data

(62) Division of application No. 08/823,434, filed on Mar. 24, 1997, now Pat. No. 5,766,238, which is a division of application No. 08/783,097, filed on Jan. 14, 1997, now Pat. No. 5,735,893, which is a division of application No. 08/556,516, filed on Nov. 13, 1995, now Pat. No. 5,603,721, which is a division of application No. 08/281,790, filed on Jul. 28, 1994, now Pat. No. 5,514,154, which is a continuation-in-part of application No. 08/164,986, filed on Dec. 9, 1993, now abandoned, which is a continuation of application No. 07/783,558, filed on Oct. 28, 1991, now abandoned.

(51) Int. Cl.
*A61F 2/06* (2006.01)
*A61F 2/00* (2006.01)
*C23F 1/02* (2006.01)

(52) U.S. Cl. ...................................................... 623/1.15
(58) Field of Classification Search ................. 623/1.15, 623/1.16
See application file for complete search history.

(56) References Cited

U.S. PATENT DOCUMENTS

| | | | |
|---|---|---|---|
| 2,070,073 A | 2/1937 | Walton |
| 2,701,559 A | 2/1955 | Cooper |
| 2,854,982 A | 10/1958 | Pagano |
| 2,854,983 A | 10/1958 | Baskin |
| 3,105,492 A | 10/1963 | Jeckel |

(Continued)

FOREIGN PATENT DOCUMENTS

| | | |
|---|---|---|
| AU | A-23784/88 | 4/1989 |
| AU | 23784/88 A | 4/1989 |
| AU | 23784/88 B | 4/1989 |
| AU | B-61333/90 | 2/1991 |
| AU | 61333/90 B | 2/1991 |

(Continued)

OTHER PUBLICATIONS

Fischman et al. "A Randomized Comparison of Coronary–Stent Placement and Balloon Angioplasty in the Treatment of Coronary Artery Disease". NEJM. 1994;331–496–501. [Retrieved from the Internet].*

Ellis, A. "The Palmaz–Schatz Stent: Clinical Applications". in: Topol, E. ed. "Textbook of Interventional Cardiology". Philadelphia. Saunders. 1994: 702–711.*

(Continued)

*Primary Examiner*—Sara Clarke

(57) ABSTRACT

The invention is directed to an expandable stent for implantation in a body lumen, such as an artery, and a method for making it from a single length of tubing. The stent consists of a plurality of radically expandable, cylindrical elements generally aligned on a common axis and interconnected by one or more interconnective elements. The individual radially expandable cylindrical elements consist of ribbon-like material disposed in an undulating pattern. Portions of the expanded stent project outwardly into engagement with the vessel wall to more securely attach the stent.

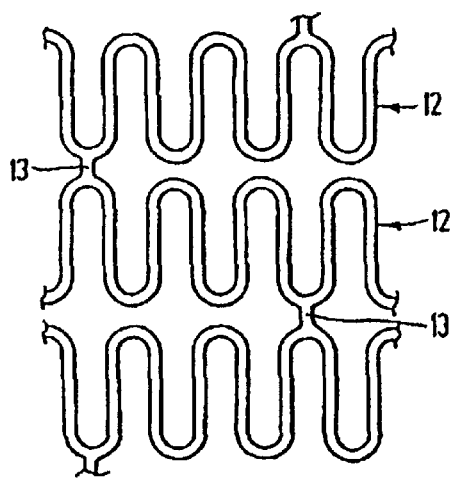

U.S. PATENT DOCUMENTS

| | | |
|---|---|---|
| 3,155,095 A | 11/1964 | Brown |
| 3,284,762 A | 11/1966 | Kompanek |
| 3,334,629 A | 8/1967 | Cohn |
| 3,420,142 A | 1/1969 | Gale et al. |
| 3,526,005 A | 9/1970 | Boskros et al. |
| 3,540,431 A | 11/1970 | Mobi-Uddin |
| 3,562,820 A | 2/1971 | Braun |
| 3,599,641 A | 8/1971 | Sheridan |
| 3,657,744 A | 4/1972 | Ersek |
| 3,713,175 A | 1/1973 | Weisman |
| 3,714,671 A | 2/1973 | Edwards et al. |
| 3,774,596 A | 11/1973 | Cook |
| 3,834,394 A | 9/1974 | Hunter et al. |
| 3,858,441 A | 1/1975 | Comeau |
| 3,868,956 A | 3/1975 | Alfidi et al. |
| 3,874,388 A | 4/1975 | King et al. |
| 3,882,845 A | 5/1975 | Bucalo |
| 3,889,685 A | 6/1975 | Miller, Jr. et al. |
| 3,893,344 A | 7/1975 | Dantigraber et al. |
| 3,894,974 A | 7/1975 | Hunter et al. |
| 3,952,747 A | 4/1976 | Kimmell, Jr. |
| 3,968,800 A | 7/1976 | Vilasi |
| 3,993,078 A | 11/1976 | Bergentz et al. |
| 4,038,702 A | 8/1977 | Sawyer |
| 4,047,252 A | 9/1977 | Liebig et al. |
| 4,056,854 A | 11/1977 | Boretos et al. |
| 4,061,134 A | 12/1977 | Samuels et al. |
| 4,065,816 A | 1/1978 | Sawyer |
| 4,076,285 A | 2/1978 | Martinez |
| 4,080,706 A | 3/1978 | Heilman et al. |
| 4,105,022 A | 8/1978 | Antoshkiw et al. |
| 4,106,129 A | 8/1978 | Carpentier et al. |
| 4,130,904 A | 12/1978 | Whalen |
| 4,140,126 A | 2/1979 | Choudhury |
| 4,159,719 A | 7/1979 | Haerr |
| 4,183,102 A | 1/1980 | Guiset |
| 4,190,909 A | 3/1980 | Ablaza |
| 4,195,637 A | 4/1980 | Grüntzig et al. |
| 4,198,982 A | 4/1980 | Fortner et al. |
| 4,214,587 A | 7/1980 | Sakura, Jr. |
| RE30,434 E | 11/1980 | Davis |
| 4,264,419 A | 4/1981 | Pryor |
| 4,276,132 A | 6/1981 | Fettel et al. |
| 4,295,464 A | 10/1981 | Shihata |
| 4,299,226 A | 11/1981 | Banka |
| 4,300,244 A | 11/1981 | Bokros |
| 4,313,231 A | 2/1982 | Koyamada |
| 4,319,363 A | 3/1982 | Ketharanathan |
| 4,323,071 A | 4/1982 | Simpson et al. |
| 4,323,994 A | 4/1982 | Coogler |
| 4,328,811 A | 5/1982 | Fogarty |
| 4,338,942 A | 7/1982 | Fogarty |
| 4,340,046 A | 7/1982 | Cox |
| 4,343,048 A | 8/1982 | Ross et al. |
| 4,343,049 A | 8/1982 | Fettel et al. |
| 4,387,952 A | 6/1983 | Slusher |
| 4,390,599 A | 6/1983 | Broyles |
| 4,402,307 A | 9/1983 | Hanson et al. |
| 4,403,612 A | 9/1983 | Fogarty |
| 4,448,195 A | 5/1984 | LeVeen et al. |
| 4,479,497 A | 10/1984 | Fogarty et al. |
| 4,483,340 A | 11/1984 | Fogarty et al. |
| 4,493,711 A | 1/1985 | Chin et al. |
| 4,494,531 A | 1/1985 | Gianturco |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,550,447 A | 11/1985 | Seiler, Jr. et al. |
| 4,553,545 A | 11/1985 | Maass et al. |
| 4,560,374 A | 12/1985 | Hammerslag |
| 4,562,596 A | 1/1986 | Kornberg |
| 4,572,186 A | 2/1986 | Gould et al. |
| 4,577,631 A | 3/1986 | Kreamer |
| 4,580,568 A | 4/1986 | Gianturco |
| 4,586,505 A | 5/1986 | Sisson et al. |
| 4,604,762 A | 8/1986 | Robinson |
| 4,616,652 A | 10/1986 | Simpson |
| 4,617,932 A | 10/1986 | Kornberg |
| 4,619,246 A | 10/1986 | Molgaard-Nielsen et al. |
| 4,619,261 A | 10/1986 | Guerriero |
| 4,641,653 A | 2/1987 | Rockey |
| 4,643,184 A | 2/1987 | Mobin-Uddin |
| 4,647,416 A | 3/1987 | Seiler, Jr. et al. |
| 4,649,922 A | 3/1987 | Wiktor |
| 4,650,466 A | 3/1987 | Luther |
| 4,655,771 A | 4/1987 | Wallsten |
| 4,660,559 A | 4/1987 | McGregor et al. |
| 4,660,560 A | 4/1987 | Klein |
| 4,665,918 A | 5/1987 | Garza et al. |
| 4,670,734 A | 6/1987 | Caddock |
| 4,673,409 A | 6/1987 | Van Kampen |
| 4,676,241 A | 6/1987 | Webb et al. |
| 4,680,031 A | 7/1987 | Alonso |
| 4,681,110 A | 7/1987 | Wiktor |
| 4,699,611 A | 10/1987 | Bowden |
| 4,704,126 A | 11/1987 | Baswell et al. |
| 4,705,517 A | 11/1987 | DiPisa, Jr. |
| 4,706,671 A | 11/1987 | Weinrib |
| 4,710,181 A | 12/1987 | Fuqua |
| 4,723,549 A | 2/1988 | Wholey et al. |
| 4,731,054 A | 3/1988 | Billeter et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,771,773 A | 9/1988 | Kropf |
| 4,771,777 A | 9/1988 | Horzewski et al. |
| 4,775,426 A | 10/1988 | Murley et al. |
| 4,776,337 A | 10/1988 | Palmaz |
| 4,787,899 A | 11/1988 | Lazarus |
| 4,793,348 A | 12/1988 | Palmaz |
| 4,794,928 A | 1/1989 | Kletschka |
| 4,795,458 A | 1/1989 | Regan |
| 4,800,882 A | 1/1989 | Gianturco |
| 4,813,925 A | 3/1989 | Anderson, Jr. et al. |
| 4,823,814 A | 4/1989 | Drogendijk et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,856,516 A | 8/1989 | Hillstead |
| 4,869,714 A | 9/1989 | Deininger et al. |
| 4,870,966 A | 10/1989 | Dellon et al. |
| 4,875,480 A | 10/1989 | Imbert |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,892,541 A | 1/1990 | Alonso |
| 4,893,623 A | 1/1990 | Rosenbluth |
| 4,902,289 A | 2/1990 | Yannas |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |

| Patent No. | Date | Inventor |
|---|---|---|
| 4,923,464 A | 5/1990 | DiPisa, Jr. |
| 4,943,346 A | 7/1990 | Mattelin |
| 4,950,227 A | 8/1990 | Savin et al. |
| 4,954,126 A | 9/1990 | Wallsten |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,032 A | 2/1991 | Sugiyama et al. |
| 4,994,071 A | 2/1991 | MacGregor |
| 4,994,077 A | 2/1991 | Dobben |
| 4,998,539 A | 3/1991 | Delsanti |
| 4,998,923 A | 3/1991 | Samson et al. |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,399 A | 4/1992 | Lazarus |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,201,901 A | 4/1993 | Harada et al. |
| 5,217,482 A | 6/1993 | Keith |
| 5,222,971 A | 6/1993 | Willard et al. |
| RE34,327 E | 7/1993 | Kreamer |
| 5,226,913 A | 7/1993 | Pinchuk |
| 5,234,456 A | 8/1993 | Silvestrini |
| 5,236,447 A | 8/1993 | Kubo et al. |
| 5,242,394 A | 9/1993 | Tremulis |
| 5,242,399 A | 9/1993 | Lau et al. |
| 5,242,452 A | 9/1993 | Inoue |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,848 A | 2/1994 | Schmitt |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,306,286 A | 4/1994 | Stack et al. |
| 5,314,444 A | 5/1994 | Gianturco |
| 5,314,472 A | 5/1994 | Fontaine |
| 5,330,500 A | 7/1994 | Song |
| 5,342,348 A | 8/1994 | Kaplan |
| 5,344,426 A | 9/1994 | Lau et al. |
| 5,354,308 A | 10/1994 | Simon et al. |
| 5,354,309 A | 10/1994 | Schnepp-Pesch et al. |
| 5,356,433 A | 10/1994 | Rowland et al. |
| 5,360,401 A | 11/1994 | Turnland |
| 5,368,566 A | 11/1994 | Crocker |
| 5,372,600 A | 12/1994 | Beyar et al. |
| 5,378,239 A | 1/1995 | Termin et al. |
| 5,382,261 A | 1/1995 | Palmaz |
| 5,383,892 A | 1/1995 | Cardon et al. |
| 5,397,345 A | 3/1995 | Lazarus |
| 5,405,378 A | 4/1995 | Strecker |
| 5,411,552 A | 5/1995 | Andersen et al. |
| 5,421,955 A | 6/1995 | Lau et al. |
| 5,423,745 A | 6/1995 | Todd et al. |
| 5,423,885 A | 6/1995 | Williams |
| 5,443,496 A | 8/1995 | Schwartz et al. |
| 5,445,646 A | 8/1995 | Euteneuer et al. |
| 5,449,373 A | 9/1995 | Pinchasik et al. |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,507,767 A | 4/1996 | Maeda et al. |
| 5,507,768 A | 4/1996 | Lau et al. |
| 5,507,771 A | 4/1996 | Gianturco |
| 5,514,154 A | 5/1996 | Lau et al. |
| 5,527,336 A | 6/1996 | Rosenbluth et al. |
| 5,545,132 A | 8/1996 | Fagan et al. |
| 5,549,635 A | 8/1996 | Solar |
| 5,549,663 A | 8/1996 | Cottone, Jr. |
| 5,554,181 A | 9/1996 | Das |
| 5,556,413 A | 9/1996 | Lam |
| 5,562,728 A | 10/1996 | Lazarus et al. |
| 5,569,295 A | 10/1996 | Lam |
| 5,571,135 A | 11/1996 | Fraser et al. |
| 5,591,197 A | 1/1997 | Orth et al. |
| 5,591,198 A | 1/1997 | Boyle et al. |
| 5,603,721 A | 2/1997 | Lau et al. |
| 5,618,299 A | 4/1997 | Khosravi et al. |
| 5,618,301 A | 4/1997 | Hauenstein et al. |
| 5,626,604 A | 5/1997 | Cottone, Jr. |
| 5,653,690 A | 8/1997 | Booth et al. |
| 5,653,691 A | 8/1997 | Rupp et al. |
| 5,653,727 A | 8/1997 | Wiktor |
| 5,669,936 A | 9/1997 | Lazarus |
| 5,674,278 A | 10/1997 | Boneau |
| 5,707,386 A | 1/1998 | Schnepp-Pesch et al. |
| 5,716,396 A | 2/1998 | Williams, Jr. |
| 5,718,713 A | 2/1998 | Frantzen |
| 5,720,726 A | 2/1998 | Marcadis et al. |

| | | | |
|---|---|---|---|
| 5,725,570 A | 3/1998 | Heath | |
| 5,728,158 A | 3/1998 | Lau et al. | |
| 5,733,303 A | 3/1998 | Israel et al. | |
| 5,733,325 A | 3/1998 | Robinson et al. | |
| 5,735,893 A | 4/1998 | Lau et al. | |
| 5,755,771 A | 5/1998 | Penn et al. | |
| 5,755,776 A | 5/1998 | Al-Saadon | |
| 5,759,192 A | 6/1998 | Saunders | |
| 5,766,238 A | 6/1998 | Lau et al. | |
| 5,776,161 A | 7/1998 | Globerman | |
| 5,780,807 A | 7/1998 | Saunders | |
| 5,782,855 A | 7/1998 | Lau et al. | |
| 5,800,509 A | 9/1998 | Boneau | |
| 5,800,521 A | 9/1998 | Orth | |
| 5,800,526 A | 9/1998 | Anderson et al. | |
| 5,810,871 A | 9/1998 | Tuckey et al. | |
| 5,817,152 A | 10/1998 | Birdsall et al. | |
| 5,830,217 A | 11/1998 | Ryan | |
| 5,833,699 A | 11/1998 | Chuter | |
| 5,836,964 A | 11/1998 | Richter et al. | |
| 5,836,965 A | 11/1998 | Jendersee et al. | |
| 5,843,120 A | 12/1998 | Israel et al. | |
| 5,843,164 A | 12/1998 | Frantzen et al. | |
| 5,843,175 A | 12/1998 | Frantzen | |
| 5,868,782 A | 2/1999 | Frantzen | |
| 5,879,381 A | 3/1999 | Moriuchi et al. | |
| 5,879,382 A | 3/1999 | Boneau | |
| 5,891,190 A | 4/1999 | Boneau | |
| 5,893,852 A | 4/1999 | Morales | |
| 5,902,332 A | 5/1999 | Schatz | |
| 5,911,732 A | 6/1999 | Hojeibane | |
| 5,913,897 A | 6/1999 | Corso, Jr. et al. | |
| 5,925,061 A | 7/1999 | Ogi et al. | |
| 5,935,162 A | 8/1999 | Dang | |
| 5,972,018 A | 10/1999 | Israel et al. | |
| 5,980,553 A | 11/1999 | Gray et al. | |
| 5,984,964 A | 11/1999 | Roberts et al. | |
| 5,997,468 A | 12/1999 | Wolff et al. | |
| 6,030,413 A | 2/2000 | Lazarus | |
| 6,056,776 A | 5/2000 | Lau et al. | |
| 6,066,167 A | 5/2000 | Lau et al. | |
| 6,066,168 A | 5/2000 | Lau et al. | |
| 6,146,358 A | 11/2000 | Rowe | |
| 6,309,412 B1 | 10/2001 | Lau et al. | |
| 6,344,053 B1 | 2/2002 | Boneau | |
| 6,432,133 B1 | 8/2002 | Lau et al. | |
| 6,485,511 B2 | 11/2002 | Lau et al. | |
| 6,511,504 B1 | 1/2003 | Lau et al. | |

FOREIGN PATENT DOCUMENTS

| | | | |
|---|---|---|---|
| AU | 61333/90 A | 2/1991 | |
| AU | 53198/94 B | 3/1994 | |
| AU | B-53198/94 | 3/1994 | |
| DE | 3823-060 A1 | 1/1989 | |
| DE | 3724479 A1 | 2/1989 | |
| DK | 04177928 | 12/1996 | |
| EP | 0177330 | 4/1986 | |
| EP | 0177330 A2 | 4/1986 | |
| EP | 0183372 | 6/1986 | |
| EP | 0183372 A1 | 6/1986 | |
| EP | 0190543 A1 | 8/1986 | |
| EP | 0190543 | 8/1986 | |
| EP | 0221570 | 5/1987 | |
| EP | 0221570 A2 | 5/1987 | |
| EP | 0274846 | 7/1988 | |
| EP | 0274846 A1 | 7/1988 | |
| EP | 0282175 A1 | 9/1988 | |
| EP | 0282175 | 9/1988 | |
| EP | 0290138 | 11/1988 | |
| EP | 0290138 A2 | 11/1988 | |
| EP | 0308512 | 3/1989 | |
| EP | 0308512 A1 | 3/1989 | |
| EP | 0312852 | 4/1989 | |
| EP | 0312852 A1 | 4/1989 | |
| EP | 0335341 | 10/1989 | |
| EP | 0335341 A1 | 10/1989 | |
| EP | 0338816 | 10/1989 | |
| EP | 0338816 A2 | 10/1989 | |
| EP | 0357003 | 3/1990 | |
| EP | 0357003 A2 | 3/1990 | |
| EP | 0364787 | 4/1990 | |
| EP | 0364787 A1 | 4/1990 | |
| EP | 0372789 A2 | 6/1990 | |
| EP | 0372789 | 6/1990 | |
| EP | 0380668 | 8/1990 | |
| EP | 0380668 A1 | 8/1990 | |
| EP | 0407951 A2 | 1/1991 | |
| EP | 0407951 | 1/1991 | |
| EP | 0408245 | 1/1991 | |
| EP | 0408245 A1 | 1/1991 | |
| EP | 0417928 | 3/1991 | |
| EP | 0417928 B1 | 3/1991 | |
| EP | 0421729 A2 | 4/1991 | |
| EP | 0421729 | 4/1991 | |
| EP | 0423916 A1 | 4/1991 | |
| EP | 0423916 | 4/1991 | |
| EP | 0428471 | 5/1991 | |
| EP | 0428471 A2 | 5/1991 | |
| EP | 0483372 | 5/1992 | |
| EP | 0483372 A1 | 5/1992 | |
| EP | 0517075 | 12/1992 | |
| EP | 0517075 A1 | 12/1992 | |
| EP | 0540290 A2 | 5/1993 | |
| EP | 0 540 290 B1 | 5/1993 | |
| EP | 0540290 B1 | 5/1993 | |
| EP | 0729767 B1 | 9/1996 | |
| EP | 0729767 | 9/1996 | |
| EP | 0 417 928 B1 | 11/1996 | |
| EP | 0 417 928 B1 | 11/1998 | |
| GB | 1205743 | 9/1970 | |
| GB | 1583192 | 1/1981 | |
| GB | 2070490 | 9/1981 | |
| GB | 2070490 A | 9/1981 | |
| GB | 2092894 A | 8/1982 | |
| GB | 2092894 | 8/1982 | |
| GB | 2135585 | 11/1983 | |
| JP | 58-501458 F | 9/1983 | |
| JP | 58-501458 | 9/1983 | |
| JP | 62-235496 | 10/1987 | |
| JP | 62-235496 A | 10/1987 | |
| JP | 63-214264 | 9/1988 | |
| JP | 63-214264 E | 9/1988 | |
| JP | 1-145076 A | 6/1989 | |
| JP | 1-145076 | 8/1989 | |
| JP | 1-299550 | 12/1989 | |
| JP | 2-174859 A | 7/1990 | |
| JP | 2-174859 | 7/1990 | |
| JP | 2-255157 B | 10/1990 | |
| JP | 2-255157 | 10/1990 | |
| JP | 3-9745 | 1/1991 | |
| JP | 3-9746 | 1/1991 | |
| JP | 3-009745 A | 1/1991 | |
| JP | 3-009746 A | 1/1991 | |
| JP | 4-25755 | 2/1992 | |
| SU | 1457921 A1 | 2/1989 | |
| WO | WO 83/03752 | 11/1983 | |
| WO | WO 83/03752 A1 | 11/1983 | |
| WO | WO 84/00121 A1 | 1/1984 | |
| WO | WO 84/00121 | 1/1984 | |
| WO | WO 89/08433 | 2/1989 | |
| WO | WO 89/01798 A1 | 3/1989 | |
| WO | WO 89/01798 | 3/1989 | |

| | | |
|---|---|---|
| WO | WO 89/08433 A1 | 9/1989 |
| WO | WO 91/07139 A1 | 5/1991 |
| WO | WO 91/07139 | 5/1991 |
| WO | WO 91/17720 | 11/1991 |
| WO | WO 91/17720 A1 | 11/1991 |
| WO | WO 92/05734 A1 | 4/1992 |
| WO | WO 92/06734 | 4/1992 |
| WO | WO 92/09246 | 6/1992 |
| WO | WO 92/09246 A1 | 6/1992 |
| WO | WO 94/17754 A1 | 8/1994 |

OTHER PUBLICATIONS

Weinhaus et al. "Anatomy of the Human Heart." in Iaizzo, Paul A. (Ed.), "Handbook of Cardiac Anatomy, Physiology, and Devices" (Totowa, N.J., Humana Press, 2005), pp. 51, 72–75,78, ISBN: 978–1–59259–835–9 (Online) [retrieved Dec. 4, 2007]. Retrieved from Springerlink.com, DOI 10.1007/978–1–59259–835–9_4.*

Netter, Frank. "Atlas of Human Anatomy". Summit, N.J., Novartis, 1997. plate 248.*

Cantor, Warren J., M.D., et al. "Failed coronary stent deployment," American Heart Journal, vol. 136, No. 6, Dec. 1998, pp. 1088–1095 USA.

Netter, Frank H., M.D., Veins of Posterior Abdominal Wall, Plate 248, Atlas of Human Anatony, 1998 USA.

Foran, J.P.M., MB, BS, MRCP, et al., "Bail–Out Coronary Stenting in an Extremely Tortuous Right Coronary Artery With the Palmaz–Schatz Stent and Teleguide Sheath," Catheterization and Cardiovascular Diagnosis, vol. 30, pp. 33–36, 1993 USA.

Levine, Glenn, M.D., et al., "Use of Bare–Mounted Palmaz–Schatz Stents Employing the Stent Saddle Technique on the Delivery Balloon: A Single Center Experience," Catheterization and Cardiovascular Interventions, vol. 41, pp. 361–368, 1997 USA.

Kasaoka, Shuni, M.D., et al., "Comparison of the Sheath Delivery System Versus Bare Stenting for Coronary Stent Implantation," Catheterization and Cardiovascular Interventions, vol. 43, pp. 386–394, 1998 USA.

Lee, Benjamin I., M.D., "Bent Stents: A Method to Facilitate Delivery of the Palmaz–Schatz Stent in Tortuous and Rigid Coronary Arteries," Catheterization and Cardiovascular Interventions, vol. 44, pp. 341–344, 1998 USA.

Bartorelli, Antonio L., M.D., et al., "Successful Stent Delivery With Deep Seating of 6 French Guiding Catheters in Difficult Coronary Anatomy," Catheterization and Cardiovascular Interventions, vol. 48, pp. 279–284, 1999 USA.

Wong, Philip H.C., MBBS, FRCP, FACC, et al., "Clinical Application of a New Palmaz–Schatz Coronary Stent Delivery System With a Short (8 mm) Nonarticulated Stent," Catheterization and Cardiovascular Diagnosis, 1995 vol. 34, pp. 82–87 USA.

Fischman, David L., et al., "The Palmaz–Schatz™ stent," Advances in Quantitative Coronary Arteriography, pp. 553–566, 1993 USA.

Ellis, Stephen G., "The Palmaz–Schatz Stent: Clinical Applications," Textbook of Interventional Cardiology, Chapter 40, pp. 702–711, 1994 USA.

Fischman, David L., et al., "A Randomized Comparison of Coronary–Stent Placement and Balloon Angioplasty in the Treatment of Coronary Artery Disease," The New England Journal of Medicine, vol. 331, No. 8, pp. 496–501, Aug. 25, 1994 USA.

"70th Scientific Assembly and Annual Meeting: Scientific Program," Radiology, Washington, D.C.: Nov. 25–30, 1984, Special Edition, vol. 153(P).

"$72^{nd}$ Scientific Assembly and Annual Meeting: RSNA Scientific Program,", Radiology, Chicago: Nov. 30–Dec. 5, 1986, Special Edition, Vol. 161(P).

"Program: Day 2 (Nov. 18) The Radiological Society of North America," Radiology, Chicago: Nov. 30–Dec. 5, 1986, Special Edition, vol. 161(P).

Alvarado, R. et al., "Evaluation of Polymer–Coated Balloon–Expandable Stents in Bile Ducts," Radiology, 170, 3: 975–978, Mar. 1989.

American Heart Association $61^{st}$ Scientific Sessions. Abstract Form. "A New Percutaneous Expandable Stent."

Baier, R., et al., "Initial Events in Interaction of Blood with a Foreign Surface," Journal of Biomedical Material Research, 3: 191–206, 1969.

Balko, A., et al., "Transfemoral Placement of Intraluminal Polyurethane Prosthesis for Abdominal Aortic Aneurysm," Journal of Surgical Research, 40: 305–309, 1986.

Becker, G., et al., "Early Experience with the Palmaz Stent in Human Illiac Angloplasty," Indiana Medicine, 286–292, Apr. 1989.

Becker, G., et al., "Simultaneous Angioplasty and Intraluminal Grafting with the Palmaz Expandable Intraluminal Graft," $72_{nd}$ Scientific Assembly and Annual Meeting of the Radiological Society of North America, Chicago, Nov./Dec. 1986.

Bonzel, T., et al., "The Sliding Rail System (Monorail): Description of a New Technique for Intravascular Instrumentation and its Application to Coronary Angioplasty," Kardologie, Supplement 6: 119–122;1987.

Campbell, C., et al., "Expanded Microporous Polytetrafluoroethylene as a Vascular Substitute: A Two Year Follow–up," Surgery, 85, No. 2: 177–183, Feb. 1979.

Carrasco, C., et al., "Expandable Biliary Endoprosthesis: An Experimental Study," American Journal of Roentgenology, 145: 1279–1281, Dec. 1985.

Castaneda–Zuniga, W., ed., Tranluminal Angioplasty, 1983.

Charnsangavej, C., et al., "A New Expandable Metallic Stent for Dilaton of Stenotic Tubular Structures: Experimental and Clinical Evaluation," Houston Medical Journal, 3, No. 2: 41–51, 1987.

Charnsangavej, C., et al., "Endovascular Stent for Use in Aortic Dissection: An in Vitro Experiment," Radiology, 157: 323–324,1985.

Charnsangavej, C., et al., "Stenosis of the Vena Cava: Preliminary Assessment of Treatment with Expandable Metallic Stents," Radiology, 161: 295–298, 1986.

Cimochowski, G., et al., "Greenfield Filter Versus Mobin–Uddin Umbrella," Journal of Thoracic and Cardiovascular Surgery, 79, No. 3: 358–365, Mar. 1980.

Coons, H., et al, "Large–Bore, Long Biliary Endoprostheses (Biliary Stents) for Improved Drainage," Radiology, 148, No. 1: 89–94, Jul. 1983.

Cope, C., "Balloon Dilatation of Closed Mesocaval Shunts," American Journal of Roentgenology, 135: 989–993, Nov. 1980.

Cragg, A., et al., "A New Percutaneous Vena Cava Filter," American Journal of Roentgenology, 141: 601–604, Sep. 1983.

Cragg, A., et al., "Non–Surgical Placement of Arterial Endoprostheses: A New Technique Using Nitinol Wire," Radiology, 147: 261–263, 1983.

Cragg, A., et al., "Percutaneous Arterial Grafting," *Radiology*, 150, No. 1: 45–49, Jan. 1984.

Culverwell, M., "Angioplasty Stents May Prevent Restenosis," *Cardio*, 11–13, Jan. 1987.

Dalessandri, K., et al., "The Effect of Lumbar Sympathectomy on Postsynaptic Vascular Smooth Muscle Response in the Lower Limb in Dogs," *Cardiovascular and Interventional Radiology*, 11:82–85, 1988.

De Palma, V., et al., "Investigation of Three Surface Properties of Several Metals and their relation to Blood Compatibility," *Journal of Biomedical Materials Research Symposium*, 3: 37–75, 1972.

Denny, D., et al., "Percutaneous Kimray–Greenfield Filter Placement by Femoral Vein Puncture," *American Journal of Roentgenology*, 145: 827–829, Oct. 1985.

Deriu, G., et al., "The Rationale for Patch–Graft Angioplasty After Carotid Endarterectomy: Early and Long–Term Follow–Up," *Stroke*, 15: No. 6: 972–979, Nov. 1984.

Dichek, D.A., et al., "Seeding of Intravascular Stents with Genetically Engineered Endothelial Cells," *Circulation*, 80: 1237–1353, 1989.

Dorland's Illustration Medical Dictionary, Twenty–Sixth Edition, W.B. Saunders Company, pp. 675, 759, Undated.

Dotter, C., "Interventional Radiology—Review of an Emerging Field," *Seminars in Roentgenology*, 16, No. 1, Jan. 1981.

Dotter, C., "Transluminally–placed Coilspring Endarterial Tube Grafts: Long–term Patency In Canine Popliteal Artery," *Investigative Radiology*, 4: 329–332, 1969.

Dotter, C., et al., "Transluminal Expandable Nitinol Coil Stent Grafting: Preliminary Report," *Radiology*, 147: 259–260, 1983.

Dotter, C., et al., "Transluminal Treatment of Arteriosclerotic Obstruction," *Circulation*, 30: 654–670, Nov. 1964.

Duprat, G., et al, "Self–expanding Metallic Stents for Small Vessels: An Experimental Evaluation," *Radiology*, 192: 469–472, 1987.

Duprat, G., et al., "Flexible Balloon–expanded Stent for Small Vessels, Work in Progress," *Radiology*, 162: 276–278, 1987.

Edwards, W., "Arterial Grafts," *Archives of Surgery*, 113, No. 9: 1225–1233, Nov. 1978.

Eichelter, P., et al., Prophytaxis of Pulmonary Embolism, *Archives of Surgery*, 97: 348–356, Aug. 1968.

Fallone, B., "Elastic Characteristics of the Self–Expanding Metallic Stents," *Investigative Radiology*, 23: 370–376, 1988.

Finci, L., et al., "Percutaneous Transluminal Coronary Angioplasty of Bifurcation Narrowing Using the Kissing Wire Monorail Balloon Technique," *The American Journal of Cardiology*, Apr. 1987.

Fogarty, T., et al., "Adjunctive Intraoperative Arterial Dilation: Simplified Instrumentation Technique," *Archives of Surgery*, 116: 1391–1398, 1981.

Fogarty, T., et al., "Current Status of Dilatation Catheters and Guiding Systems," *American Journal of Cardiology*, 53, No. 12: 97C–100C, Jun. 1984.

Fogarty, T., et al., "Intraoperative Coronary Artery Balloon–Catheter Dilation," *American Heart Journal*, 107, No. 4: 845–851, 1984.

Frimberger, E., "Expanding Spiral—A New Type of Prosthesis for the Palliative Treatment of Malignant Esophageal Stenoses," *Endoscopy*, 15: 213–214, 1983.

Furui, S., et al., "Hepatic Inferior Vena Cava Obstruction: Treatment of Two Tubes With Gianturco Expandable Metallic Stents," *Interventional Radiology*, 176:665–670, 1990.

Gardner, R., et al., "The Surgical Experience and a One to Sixteen Year Follow–Up of 277 Abdominal Aortic Aneurysms," *American Journal of Surgery*, 135, No. 1: 226–230, Jan. 1978.

Goldstein, H., et al, "Transcatheter Occlusion of Abdominal Tumors," *Radiology*, 120, No. 3: 539–545, Sep. 1976.

Harries–Jones, E., et al., "Repositioning of Biliary Endoprosthesis with Gruntzig Balloon Catheters," *American Journal of Roentganology*, 138: 771–772, Apr. 1982.

Harrington, J., et al., "The Palmaz–Schatz Stent," *Handbook of Cardiovascular Interventions/Vascular Interventions*, 536–572.

Hoevels, J., et al., "Percutaneous Transhepatic Insertion of a Permanent Endoprosthesis on Obstructive Lesions of the Extrahepatic Bile Ducts," *Gastrointestinal Radiology*, 4: 367–377, 1979.

Honickman, S., et al., "Malpositioned Biliary Endoprosthesis," *Radiology*, 144: 423–425, Jul. 1982.

Hunter, J., et al., "Experimental Balloon Obstruction of the Inferior Vena Cava," *Annals of Surgery*, 171, No. 2: 315–320, Feb. 1970.

Inoue, K., et al., "Clinical Application of Transvenous Mitral Commissurotomy by a New Balloon Catheter," *Thoracic Cardiovascular Surgery*, 87, No. 3: 394–402, Mar. 1984.

Kan, J., et al., "Percutaneous Balloon Valvuloplasty: A New Method for Treating Congenital Pulmonary–Valve Stenosis," *New England Journal of Medicine*, 307, No. 9, 540–542, 1982.

Kerlan, R., et al., "A Simple Method for Insertion of Large Untapered Catheters," *American Journal of Roentgenology*, 141: 792, 1983.

Kerlan, R., et al., "Biliary Endoprostheses: Insertion Using a Combined Peroral–Transhepatic Method," *Radiology*, 150, No. 3: 828–830, 1984.

Lababidi, Z., et al., "Percutaneous Balloon Aortic Valvuloplasty: Results in 23 Patients," *American Journal of Cardiology*, 53: 194–197, Jan. 1984.

Lary, B., et al., "The Experimental Use of Steel Mesh Tubes for Replacement Arterial Segments," *AMA Archives of Surgery*, 72: 69–75, Jan. 1956.

Lawrence, D., et al., "Percutaneous Endovascular Graft: Experimental Evaluation," *Radiology*, 163:357–360, May 1987.

Lewandowski, B., et al., "The Air–Filled Hepatic Duct: The Saber Sign as an Aid to the Radiographic Diagnosis Pneumobilia," *Radiology*, 153, No. 2: 329–332, Nov. 1984.

Lund, G., et al., "A New Vena Caval Filter for Percutaneous Placement and Retrieval: Experimental Study," *Radiology*, 152, No. 2: 369–372, Aug. 1984.

Lunderquist, A., et al., "Guidewire for Percutaneous Transhepatic Cholangiography," *Radiology*, 132, No. 1: 228, Jul. 1979.

Maass, D., et al., "Radiological Follow–up of Transluminally Inserted Vascular Endoprostheses: An Experimental Study Using Expanding Spirals," *Radiology*, 152: 659–663, 1984.

Meenaghan, M., et al., "Tissue Response to Surface–Treated Tantalum Implants: Preliminary Observations in Primates," *Biomedical Materials Research*, 13, No. 4: 631–643, Jul. 1979.

Messler, R., *Joining of Materials and Structures: From Pragmatic Process to Enabling Technology*, Partial of Chapters 6, 7, 8: pp. 285, 305, 332333. 349–353, 389–393; 2004.

Mirich, D., et al., "Percutaneously Placed Endovascular Grafts for Aortic Aneurysms: Feasibility Study," *Radiology*, 170:1033–1037.

Mobin_Uddin, K., et al., "The Inferior vena Cava Umbrella Filter," *Progress in Cardiovascular Diseases*, 17, No. 5: 391–399, Mar./Apr. 1975.

Mobin_Uddin, K., et al., "Caval Interruption for Prevention of Pulmonary Embolism," *Archives of Surgery*, 99: 711–715, Dec. 1969.

Muller, D., et al., "Advances in Coronary Angioplasty: Endovascular Stents," *Coronary Artery Disease*, 1: 438, Jul./Aug. 1990.

Mullins, C., et al., "Implantation of Balloon–Expandable Intravascular Grafts by Catherization in Pulmonary Arteries and Systemic Veins," *Circulation*, 77: 188–189, 1988.

Nanda, R., et al., "Effect of Maxillary Osteotomy on Subsequent Craniofacial Growth in Adolescent Monkeys," *American Journal of Orthod.*, 83: 391–407, May 1983.

Palestrant, AJ., et al., "Comparative in Vitro Evaluation of the Nitinol Inferior Vena Cava Filter," *Radiology*, 145: 351–355, Nov. 1982.

Palmaz, J., "Balloon Expandable Intra–Arterial Stents: Effect of Antiocoagulation on Thrombus Formation," *Circulation* (Supplement Part II), 76, No. 4: 180, Oct. 1987.

Palmaz, J., "Balloon–Expandable Intravascular Stent," *American Journal of Roentgenology*, 150: 1263–1269, Jun. 1988.

Palmaz, J., "Chapter 30: Overview of Intravascular Stents," in Kim, D., et al., *Peripheral Vascular Imaging and Intervention*, 507–508, 1992.

Palmaz, J., "Die intraluminate Stent–Implantation nach Palmaz," *Radiologe*, 560–563, 1987.

Palmaz, J., "Expandable Intraluminal Vascular Graft: A Feasibility Study," *Surgery*, 2: 199–205, 1986.

Palmaz, J., et al., "Atherosclerotic Rabbit Aortas: Expandable Intraluminal Grafting," *Radiology*, 3: 723–726, 1986.

Palmaz, J., et al., "Balloon–Expandable Intraarterial Stents: Effect of Antithrombotic Medication on Thrombus Foramtion," *Pros and COns in PTA and Auxiliary Methods*, 170–178, 1989.

Palmaz, J., et al., Early Endothelisation of Balloon–expandable Stents: Experimental Observations, *Journal of Interventional Radiology*, 3: 119–124, 1988.

Palmaz, J., et al., "Expandable Intrahepatic Portacaval Shunt Stents: Early Experience in the Dog," *American Journal of Roentgenology*, 145: 821–825, 1985.

Palmaz, J., et al., "Expandable Intrahepatic Portacaval Shunt Stents in Dogs with Chronic Portal Hypertension," *American Journal of Roentgenology*, 147: 1251–1254, 1986.

Palmaz, J., et al., "Expandable Intraluminal Graft: A Preliminary Study," *Radiology*, 156: 73–77, 1985.

Palmaz, J., et al., "Intraluminal Stents in Atherosclerotic Iliac Artery Stenosis: Preliminary Report of Multicenter Study," *Radiology*, 168, No. 3: 727–731, Sep. 1988.

Palmaz, J., et al., "Normal and Stenotic Renal Arteries: Experimental Balloon–Expandable Intraluminal Stenting," *Radiology*, 164: 705–708, Sep. 1987.

Palmaz, J., et al., "Removable Biliary Endoprosthesis," *American Jouranl of Roentgenology*, 140: 812–814, Apr. 1983.

Palmaz, J., Monograph (1980).

Palmaz, J., Monograph (May 18, 1983).

Palmaz, J., *The Current Status of Vascular Prosthesis, Presentation of The Society of CV & Interventional Radiology' Twelfth Annual Course on Diagnostic Angioplasty and Interventional Radiology*, 118–120, Mar. 23–26, 1987.

Papanicolaou, N., et al., "Insertion of a Biliary Endoprosthesis Using a Balloon Dilation Catheter," *Gastrointestinal Radiology*, 10: 394–396, 1985.

Pate, J. et al., "A New Form of Vena Caval Interruption," *Annals of Surgery*, 169, No. 6, 873–880, Jun. 1969.

Puel, J., et al., "Intravascular Stents to Prevent Restenosis After Transluminal Coronary Angioplasty," *Circulation* (Supplement Part II), 76, No. 4: 0105, Oct. 1987.

Rashkind, W., et al., "Creation of an Atrial Septal Defect Without Thoracotomy: A Palliative Approach to Complete Transposition of the Great Arteries," *Journal of the American Medical Association*, 196: 173–174, Jun. 1966.

Rees, C., et al., "Anglioplasty and Stenting of Completely Occuluded Iliac Arteries," *Radiology* (Part 2), 172, No. 3, 953–959, Sep. 1989.

Rees, C., et al., "DSA in Acute Gastrointestinal Hemorrhage: Clinical and in Vitro Studies," *Radiology*, 169, No. 2, 499–503, Nov. 1988.

Rees, C., et al., "The Hemodynamic Effects of the Administration of Ionic and Nonionic Contrast Materials Into the Pulmonary Arteries of a Canine Model of Acute Pulmonary Hypertension," *Investigative Radiology*, 23, No. 3: 184–189, Mar. 1988.

Richter, G., et al., "Der Transjugusiaere Intrahepatische Portosystemische Stent–Shunt (TIPSS); Eine Neue Nichtoperative, Perkutane Methode," *Radiologe*, 29: 406–411, 1989.

Richter, G., et al., "Die Behandlung eines akuten Beckenarterienverschlusses durch Kathetertyse, Katheterdilatation und Implantation einer neuartigen metallischen Gefa.beta.ednoprothese," *Der chirurg*, 60, No. 5: 346–351, May 1989.

Ring, E., et al., "A Simple, Indwelling Biliary Endoprosthesis Made From Common Available Catheter Material," *American Journal of Roengenology*, 139: 615–617, Sep. 1982.

Roehm, J., et al., "Percutaneous Transcatheter Filter for the Interior Vena Cava," *Radiology*, 150, No. 1: 255–257, Jan. 1984.

Roland, M., Spiral Teflon Stent for Tuboplasty Involving Fimbria, *Obstetrics Gynecology*, 36: 359–362. 1970.

Rollins, N., et al., "Self–expanding Metallic Stents: Preliminary Evaluation in an Atherosclerotic Model," *Radiology*, 163, No. 3: 739–742, Jun. 1987.

Rosch, J., et al., "Experiemental Intrahepatic Portacaval Anastomosis: Use of Expandable Gianturco Stents," *Radiology*, 162: 481–485, Feb. 1987.

Rosch, J., et al., "Gianturco Expandable Stents in Experimental and Clinical Use," *Diagnostic Angiography and Interventional Radiology*, 12th Annual Course, March. 23–26, 1987.

Rosch, J., et al., "Gianturco Expandable Wire Stents in the Treatment of Superior Vena Cava Syndrome Recurring After Maximum–Tolerance Radiation," *Cancer*, 60: 1243–1246, 1987.

Rosch, J., et al., "Modified Gianturco Expandble Wire Stents in Experimental and Clinical Use," *Annales de Radiologie*, 31, No. 2: 100–103, 1987.

Rosch, J., et al., "Transjugular Intrahepatic Portacaval Shunt: An Experimental Work," *American Journal of Surgery*, 121: 588–592, May 1971.

Roubin, G., et al., "Early and Late Results of Intracoronary Arterial Stenting After Coronary Angioplasty in Dogs," *Circulation*, 4: 891–897, 1987.

Rousseau, H., et al., "Percutaneous Vascular Stent: Experimental Studies and Preliminary Clinical Results in peripheral Arterial Diseases," *Inter. Angio.*, 6: 153–161. 1987.

Rousseau, H., et al., "Self–Expanding Endovascular Prosthesis: An Experimental Study," *Radiology*, 164: 709–714, Sep. 1987.

Schatz, R., "Introduction to Intravascular Stents," *Cardiology Clinics*, 6, No. 3, 357–372, 1988.

Schatz, R., et al., "A View of Vascular Stents," *Circulation*, 79: 445–457, 1989.

Schatz, R., et al., "Balloon Expandable Intracoronary Stents in Dogs," *Circulation* (Supplemental Part II), 74: II–458, 1824, 1986, 1986.

Schatz, R., et al., "Balloon–Expandable Intracoronary Stents in the Adult Dog," *Circulation*, 76, No. 2, 450–457, 1987.

Schatz, R., et al., "Intravascular Stents for Angioplasty," *Cardio*, 27–31, Dec. 1987.

Schatz, R., et al., "New Technology in Angioplasty: Balloon–Expandable Intravascular Stents," *New Developments in Medicine*, 2, No. 2: 59–75, Sep. 1987.

Semb, B., et al., "Balloon Valvulotomy of Congenital Pulmonary Valve Stenosis with Tricuspid Valve Insufficiency," *Cardiovascular Radiology*, 2: 239–241, 1979.

Sigwart, U., et al., "Intravascular Stents to Prevent Occlusion and Restenosis After Transluminal Anglioplasty," *New England Journal of Medicine*, 316: 701–706. 1987.

Simon, M., et al., "A Vena Cava Filter Using Thermal Shape Memory Alloy," *Radiology*, 125: 89–94, Oct. 1977.

Simonds, A.K., et al., "Use of Expandable Metal Stents in the Treatment of Bronchial Obstruction," *Thorax*, 44: 680, May 1989.

Smith, D., et al., "Safe and Effective Catheter Angiography Through Prosthetic Vascular Grafts," *Radiology*, 138, No. 2: 487–488, Feb. 1981.

Solberg, S., et al., "Cold Induced Endothelial Cell Detachment in Human Sephenous Vein Grafts," *Journal of Cardiovascular*, 28, No. 5: 571–575, Sep.–Oct. 1987.

Stack, R., et al., "A New Highly Flexible Balloon–Expandable Endovascular Stents: Initial Experimental Results and Up to Six Months Follow–up," *Laser One Meeting*, Newport Beach, California, May 11–13, 1989.

Strecker, E., et al., "A New Vascular Balloon–expandable Prosthesis—Experimental Studies and First Clinical Results," *Journal of Interventional Radiology*, 3: 59–62, 1988.

Strecker, E., et al., "Perkutan Implantierbare, Durth Balloon Aufdehnbare Gefa.beta.prothese," *Dtsch Med Wschr*, 113, No. 4, 538–542;1988.

Strupp, G., et al., "Clinical and Angiographic Short and Medium Term Results After Coronary Stenting," *Z kardiol*, 81: 500, 1992 (German with English language summary).

Teplick, S., et al., "A New Biliary Endoprosthesis," *American Journal of Roentgenology*, 141: 799–801, Oct. 1983.

Topol, E., *Textbook of Interventional Cardiology*, Chapter 30, by S. Ellis, 623–632, 1990.

Toshiyuki, I., et al., "Relocatable Gianturco Expandable Metallic Stents," *Radiology*, 178: 575, Feb. 1991.

Trent, M., et al., "A Balloon–Expandable Intravascular Stent for Obliterating Experimental Aortic Dissection," *Journal of Vascular Surgery*, 11: 707–717, May 1990.

Uchida, B., et al., "Modifications of Gianturco Expandable Wire Stents," *American Journal of Roentgenology*, 150: 1185–1187, 1988.

Van Der Giessen, W., et al., "Coronary Stenting With a New, Radiopaque, Balloon–Expandable Endoprosthesis in Pigs," *Circulation*, 83: 1788–1798, 1991.

Wallace, M., et al., "Tracheobronchial Tree: Expandable Metallic Stents Used in Experimental and Clinical Applications, Work In Progress," *Radiology*, 158: 309–312, 1986.

Wright, K., et al., "Percantaneous Endovascular Stents: An Experimental Evaluation," *Radiology*, 156: 69–72, 1985.

Yoshimura, H., et al., "Afterloading Intracavitary Irradiation and Expanding Stent for Malignant Biliary Obstruction," *Radiation Medicine*, 7: 36–41, 1989.

Yoshioka, T., et al., "Development and Clinical Application of Biliary Endoprosthesis Using Expandable Metallic Stents," *Japan Radiological Society*, 48: 1183–1185, 1988.

Yoshioka, T., et al., "Expandable Metallic Biliary Endoprostheses: Preliminary Clinical Evaluation," *Radiology*, 117: 253–257, 1990.

Yoshioka, T., et al., "Self–Expanding Endovascular Graft: An Experimental Study in Dogs," *AJR*, 151: 673–676, 1988.

Priestley, K.A., et al., "First clinical experience with a new flexible low profile metallic stent and delivery system," European Heart Journal, Mar. 1996, pp. 438–444, vol. 17, U.K.

Baim, D.S., M.D., et al., "Final Results of a Randomized Trial Comparing the Multi–Link Stent With the Palmaz–Schatz Stent for Narrowings in Native Coronary Arteries," The American Journal of Cardiology, Jan. 15, 2001, pp. 157–162, vol. 87, USA.

Schatz, R.A., et al., Report of a New Articulated Balloon Expandable Intravascular Stent (ABEIS). Abstracts of the 71st Scientific Sessions, (Undated) II, 449, USA.

Credo Reference for "Edge" from the Collins English Dictionary. HarperCollins Publishers 2000.

Schatz, R.A., M.D., et al., "Clinical Experience With the Palmaz–Schatz Coronary Stent: Initial Results of a Multicenter Study," Circulation, Jan. 1991, vol. 83, No. 1, pp. 148–161, USA.

Request for Inter Partes Reexamination of U.S. Patent No. 6,432,133 dated Mar. 30, 2007 and Exhibits 1–24.

Order Granting/Denying Request for Inter Partes Reexamination dated Apr. 24, 2007.

Alvarado, R., et al., "Evaluation of Polymer–Coated Balloon–Expandable Stents in Bile Ducts," *Radiology*, 170, 3: 975–978, Mar. 1989.

Becker, G., et al., "Early Experience with the Palmaz Stent in Human Iliac Angioplasty," *Indiana Medicine*, 286–292, Apr. 1989.

Brochure; "Anomatic II Positioning Controller," printed by Anorad Corporation.

Charnsangavej, C., et al., "A New Expandable Metallic Stent for Dilation of Stenotic Tubular Structures: Experimental and Clinical Evaluation," *Houston Medical Journal*, 3, No. 2: 41–51, 1987.

Cragg, A., et al., "A New Percutaneous Vena Cava Filter," *American Journal of Roentgenology*, 141: 601–604, Sep. 1983.

Cragg, A., et al., "Percutaneous Arterial Grafting," *Radiology*, 150, No. 1: 45–49, Jan. 1984.

Dotter, C., "Interventaional Radiology—Review of an Emerging Field," *Seminars in Roentgenology*, 16, No. 1, Jan. 1981.

Eichelter, P, et al., Prophylaxis of Pulmonary Embolism, *Archives of Surgery*, 97: 348–356, Aug. 1968.

Fogarty, T., et al., "Adjunctive Intraoperative Arterial Dilaton: Simplified Instrumentation Technique," *Archives of Surgery*, 116: 1391–1398, 1981.

Gardner, R., et al., "The Surgical Experience and a One to Sixteen Year Follow–Up of 277 Abdominal Aortic Aneurysms," *American Journal of Surgery*, 135, No. 1: 226–230, Jan.1978.

Greenfield, L., et al, "A New Intracaval Filter Permitting Continued Flow and Resolution of Emboli," *Surgery*, 73, No. 4: 599–606, Apr. 1973.

Gunther, R., et al, "Percutaneous Nephropyelsotomy Using a Fine–Needle Puncture Set," *Radiology*, 132, No. 1: 228–230, Jul. 1979.

Gunther, R., et al., "Vena Caval Filter to Prevent Pulmonary Embolism Experimental Study," *Radiology*, 156, No. 2: 315–320, Aug. 1985.

Kaltenbach, M., Abstracts, *Zeitschrift fur Kardiologie*, Apr. 3, 1991 (German only).

Palmaz, J., "Chapter 30: Overview of Intravascular Stents," in Kim, D., et al., *Peripheral Vascular Imaging and Intervention*, 507–508, 1992.

Palmaz, J., et al., "Balloon Expandable Intraluminal Grafting of Normal and Abnormal Renal Arteries: Experimental Study," $72^{nd}$ *Scientific Assembly and Annual Meeting*, Radiology Society of North America, Chicago, 1–23 [plus figures], Nov. 1986.

Sigwart, U., et al., "Intravascular Stents to Prevent Occlusion and Restenosis After Transluminal Angioplasty," *New England Journal of Medicine*, 316: 701–706.

Stack, R., et al., "A New Highly Flexible Balloon–Expandable Endovascular Stent: Initial Experimental Results and Up to Six Months Follow–up," *Laser One Meeting*, Newport Beach, California, May 11–13, 1989.

Strecker, E., et al., "Perkutan Implantierbare, Durth Balloon Aufdehnbare," *Dtsch Med Wschr*, 113, No. 4, 538–542, 1988.

Notice of Medtronic Vascular, Inc. to Advanced Cardiovascular Systems, Inc. and Guidant Sales Corporation Pursuant to 35 U.S.C. § 282, *ACS v. AVE*, 98–80–SLR (D. Del.) (Jan. 10, 2005).

Trial Transcript (Liability), vol. A, *ACS v. AVE*, 98–80–SLR (D. Del.) (Feb. 7, 2005).

Trial Transcript (Liability), vol. B, *ACS v. AVE*, 98–80–SLR (D. Del.) (Feb. 8, 2005).

Trial Transcript (Liability), vol. C, *ACS v. AVE*, 98–80–SLR (D. Del.) (Feb. 9, 2005).

Trial Transcript (Liability), vol. D, *ACS v. AVE*, 98–80–SLR (D. Del.) (Feb. 10, 2005).

Trial Transcript (Liability), vol. E, *ACS v. AVE*, 98–80–SLR (D. Del.) (Feb. 11, 2005).

Medtronic's Corrected Motion for Judgment as a Matter of Law, *ACS v. AVE*, 98–80–SLR (D. Del.) (Feb. 11, 2005).

ACS's Opposition to Medtronic's Motion for Judgment as a Matter of Law on Infringement, *ACS v. AVE*, 98–80–SLR (D. Del.) (Feb. 14, 2005).

Trial Transcript (Liability), vol. F, *ACS v. AVE*, 98–80–SLR (D. Del.) (Feb. 15, 2005).

Trial Transcript (Liability), vol. G, *ACS v. AVE*, 98–80–SLR (D. Del.) (Feb. 16, 2005).

Vascular's Opening Claim Construction Brief for the Lau Patents, *ACS v. AVE*, 98–80–SLR (D. Del.) (Aug. 13, 2004).

Plaintiff's Answering Claim Construction Brief Regarding Lau Patent Terms, *ACS v. AVE*, 98–80–SLR (D. Del.) (Sep. 24, 2004).

Memorandum Opinion Granting ACS's Motion for Summary Judgment That Michael D. Boneau is Not an Inventor of the Lau Patents and That the Lau Patents are Not Invalid Under 35 U.S.C. § 102(f), *ACS v. AVE*, 98–80–SLR (D. Del.) (Jan. 5, 2005).

Memorandum Order Defining Lau Patent Terms, *ACS v. AVE*, 98–80–SLR (D. Del.) (Jan. 5, 2005).

Notice of Medtronic Vascular, Inc. to Advanced Cardiovascular Systems, Inc. and Guidant Sales Corporation Pursuant to 35 U.S.C. § 282, *ACS v. AVE*, 98–80–SLR (D. Del.).

Trial Transcript (Liablity), vol. A, *ACS v. AVE*, 98–80–SLR (D. Del.) (Feb. 7, 2005).

Trial Transcript (Liability), vol. C., *ACS v. AVE*, 98–80–SLR (D. Del.) (Feb. 9, 2005).

ACS's Motion for Judgment as a Matter of Law That the '154, '167, '168 and '133 Patents are (1) Not Invalid as Anticipated, (2) Not Invalid Under 35 U.S.C. § 112, and (3) Not Invalid as Obvious, *ACS v. AVE*, 98–80–SLR (D. Del.) (Feb. 16, 2005).

ACS's Motion for Judgment as a Matter of Law That the Accused Medtronic Products Infringe the Asserted Claims of the Lau Patents–in–Suit, *ACS v. AVE*, 98–80–SLR (D. Del.) (Feb. 16, 2005).

Trial Transcript (Liability), vol. H, *ACS v. AVE*, 98–80–SLR (D. Del.) (Feb. 17, 2005).

Trial Transcript (Liability), vol. 1, *ACS v. AVE*, 98–80–SLR (D. Del.) (Feb. 18, 2005).

Jury Verdict, *ACS v. AVE*, 98–80–SLR (D. Del.) (Feb. 18, 2005).

Medtronic's Renewed Motion for Judgment as Matter of Law, *ACS v. AVE*, 98–80–SLR (D. Del.) (Apr. 18, 2005).

Trial Transcript (Inequitable Conduct), *ACS v. AVE*, 98–80–SLR (D. Del.) (Jun. 7, 2005).

Trial Transcript (Inequitable Conduct), *ACS v. AVE*, 98–80–SLR (D Del.) (Jun. 8, 2005).

ACS's Response to Medtronic's Renewed Motion for Judgment as a Matter of Law, *ACS v. AVE*, 98–80–SLR (D. Del.) (Jun. 17, 2005).

Medtronic's Reply Brief in Support of Its Motion for Judgment as a Matter of Law, *ACS v. AVE*, 98–80–SLR (D. Del.) (Jun. 18, 2005).

Medtronic's Opening Post–Trial Brief on ACS's Inequitable Conduct Before the U.S. Patent and Trademark Office, *ACS v. AVE*, 98–80–SLR (D. Del.) (Jul. 28, 2005).

ACS's Post Trial Brief in Response to Medtronic's Allegations of Inequitable Conduct, *ACS v. AVE*, 98–80–SLR (D. Del.) (Sep. 19, 2005).

Medtronic's Reply Post–Trial Brief on ACS's Inequitable Conducty Before the U.S. Patent and Trademark Office, *ACS v AVE*, 98–80–SLR (D. Del.) (Oct. 7, 2005).

Docket, *ACS v. SciMed*, 98–1108 (S.D. Indiana) (Undated).

Memorandum of Law In Support of Plaintiff's Proposed Construction of Patent Claims, *ACS v. SciMed*, 98–1108 (S.D. Indiana) (Jul. 29, 1999).

Defendant's Pre–Markman Hearing Memorandum on Claim Construction, *ACS v. SciMed*, 98–1108 (S.D. Indiana) (Jul. 29, 1999).

Defendant's Memorandum in Opposition to Plaintiffs' Proposed Construction of Patent Claims, *ACS v. SciMed*, 98–1108 (S.D. Indiana) (Aug. 12, 1999).

Memorandum of Law in Reply to Defendants' Pre–Markman Hearing Memorandum on Claim Construction, *ACS v. SciMed*, 98–1108 (S.D. Indiana) (Aug. 12, 1999).

Expert Witness Report of John F. Witherspoon, *ACS v. SciMed*, 98–1108 (S.D. Indiana) (Sep. 27, 1999).

Expert Report of Dr. David Cumberland, *ACS v. SciMed*, 98–1108 (S.D. Indiana) (Sep. 27, 1999).

Entry on Claim Construction Issues, *ACS v. SciMed*, 98–1108 (S.D. Indiana) (Oct. 15, 1999).

Supplemental Expert Report of Dr. C. Forbes Dewey, Jr., *ACS v. SciMed*, 98–1108 (S.D. Indiana) (Nov. 12, 1999).

Memorandum in Support of Defendants' Motion for Additional Findings on Certain Claim Construction Issues and Reconsideration of One Issue, *ACS v. SciMed*, 98–1108 (S.D. Indiana) (Nov. 19, 1999).

Supplement to Defendants' Memorandum in Support of Their Motion for Additional Findings on Claim Construction Issues and Reconsideration of One Issue, *ACS v. SciMed*, 98–1108 (S.D. Indiana) (Dec. 1, 1999).

Memorandum of Law in Opposition to Defendants' Motion for Additional Findings on Claim Construction Issues and Reconsideration of One Issue, *ACS v. SciMed*, 98–1108 (S.D. Indiana) (Dec. 6, 1999).

Reply Memorandum in Support of Defendants' Motion for Additional Findings on Claim Construction Issues and Reconsideration of One Issue, *ACS v. SciMed*, 98–1108 (S.D. Indiana) (Dec. 15, 1999).

Memorandum of Law in Support of Guidant/ACS's Motion for Partial Summary Judgment Against Defendants' Affirmative Defense of Inequitable Conduct in Obtaining the Patents in Suit, *ACS v. SciMed*, 98–1108 (S.D. Indiana) (Dec. 15, 1999).

Defendants Notice to the Court that the Issue Raised by Plaintiffs' Motion for Partial Summary Judgment Regarding Inventorship by Michael Boneau is Moot, *ACS v. SciMed*, 98–1108 (S.D. Indiana) (Dec. 22, 1999).

Reply Memorandum of Law in Further Support of Plaintiffs' Motion for Partial Summary Judgment Against Defendants' Affirmative Defense of Inequitable Conduct Concerning Michael Boneau, *ACS v. SciMed*, 98–1108 (S.D. Indiana) (Dec. 29, 1999).

Defendants SciMed Life Systems, Inc. and Boston Scientific Corporation's Notice Pursuant to 35 U.S.C. §282, *ACS v. SciMed*, 98–1108 (S.D. Indiana) (Jan. 21, 2000).

Order, *ACS v. SciMed*, 98–1108 (S.D. Indiana) (Feb. 9, 2000).

Entry on Plaintiff's Motion for Partial Summary Judgment on Defendants' Affirmative Defense of Inequitable Conduct in Obtaining the Patents in Suit, *ACS v. SciMed*, 98–1108 (S.D. Indiana) (Feb. 9, 2000).

Entry on Defendants' Motion for Supplemental Claim Construction, *ACS v. SciMed*, 98–1108 (S.D. Indiana) (Feb. 9, 2000).

Motion to Withdraw Defendants' Motion for Summary Judgment of Invalidity, *ACS v. SciMed*, 98–1108 (S.D. Indiana) (May 18, 2000).

Order Granting Moton to Withdraw Defendants' Motion for Summary Judgment of Invalidity, *ACS v. SciMed*, 98–1108 (S.D. Indiana) (May 19, 2000).

Brief for Plaintiffs—Appellants Advanced Cardiovascular Systems, Inc. and Guidant Sales Corporation, *ACS v. SciMed*, Appeal No. 00–1454 (Fed. Cir.) (Sep. 1, 2000).

Brief for Defendants—Appellees SciMed Life Systems, Inc. and Boston Scientific Corporation, *ACS v. SciMed*, Appeal No. 00–1454 (Fed. Cir.) (Oct. 30, 2000).

Reply Brief for Plaintiffs—Appellants Advanced Cardiovascular Systems, Inc. and Guidant Sales Corporation, *ACS v. SciMed*, Appeal No. 00–1454 (Fed. Cir.) (Nov. 29, 2000).

Decision, *ACS v. SciMed*, Appeal No. 00–1454 (Fed. Cir.) (Aug. 6, 2001).

Notice of Opposition, EP 0 807 424 Opposition Proceedings (Apr. 21, 2000).

Notice of Opposition, EP 0 807 424 Opposition Proceedings (May 3, 2000).

Response to Notices of Opposition, EP 0 807 424 Opposition Proceedings Feb. 7, 2001).

Reply to Response to Notices of Oppositions, EP 0 807 424 Opposition Proceedings (Jun. 18, 2001).

Remarks Regarding Response to Opposition, EP 0 807 424 Opposition Proceedings May 16, 2002).

Response to Remarks Regarding Response to Opposition, EP 0 807 424 Opposition Proceedings (May 17, 2002).

Facts and Submissions (Grounds for Decision), EP 0 807 424 Opposition Proceedings (Jul. 4, 2002).

Minutes of oral proceedings and decision with corresponding documents, EP 0 807 424 Opposition Proceedings (Jul. 18, 2002).

Notice of Opposition, EP 0 807 424 Opposition Proceedings (Aug. 19, 2002).

Notice of Appeal, EP 0 807 424 Opposition Proceedings (Sep. 17, 2002).

Submission regarding Grounds of Appeal, EP 0 807 424 Opposition Proceedings (Nov. 28, 2002).

Claims, EP 0 807 424 Opposition Proceedings (Nov. 29, 2002).

Response to Submission Requesting Appeal, EP 0 807 424 Opposition Proceedings (Jun. 16, 2003).

Preliminary Assessment of Appeal by Technical Board of Appeal, EP 0 807 424 Opposition Proceedings (Jan. 30, 2004).

Reponse to Preliminary Assessment of Appeal by Technical Board of Appeal by Opponent, EP 0 807 424 Opposition Proceedings (Jun. 1, 2004).

Response to Preliminary Assessment of Appeal by Technical Board of Appeal by Patentee, EP 0 807 424 Opposition Proceedings (Jun. 7, 2004).

Minutes of oral proceedings and decision of Technical Board of Appeal, EP 0 807 424 Oppositon Proceedings (Jul. 8, 2004).

Notification of decision, EP 0 807 424 Opposition Proceedings (Aug. 12, 2004).

Maintenance of the Patent with the Documents Specified in the Final Decision, EP 0 807 424 Opposition Proceedings (Aug. 20, 2004).

Decision to Maintain the European Patent in Amended Form, EP 0 807 424 Opposition Proceedings (Dec. 15, 2004).

Termination of the opposition proceedings with maintenance of patent (Jan. 28,2005).

Notice of Opposition, EP 0 504 290 Opposition Proceedings (Oct. 22, 1998).

Notice of Opposition, EP 0 504 290 Opposition Proceedings (Oct. 23, 1998).

Letter enclosing new citation to Oct. 23, 1998 Opposition by Terumo, EP 0 504 290 Opposition Proceedings (Dec. 21, 1998).

Reply of Patent Proprietor to Notices of Opposition, EP 0 504 290 Opposition Proceedings (Jun. 14, 1999).

Letter Responding to Patentee's Jun. 14, 1999 Letter by Opponent Dr. Schiemdl with Attachments, EP 0 504 290 Opposition Proceedings (Oct. 18, 1999).

Reply to DOBS by Novis SRl, EP 0 504 290 Opposition Proceedings (Jan. 5, 2000).

Letter for Proprietor enclosing Declaration of Gary Schiederman and First Auxiliary Request, EP 0 504 290 Opposition Proceedings (Aug. 17, 2000).

Minutes of Oral Proceedings and Decision, EP 0 504 290 Opposition Proceedings (Oct. 24, 2000).

Claims, EP 0 504 290 Opposition Proceedings (Oct. 24, 2000).

Opposition Divisions' Decision revoking EP '290, EP 0 504 290 Opposition Proceedings (Oct. 24, 2000).

Statements of Grounds of Appeal, EP 0 504 290 Opposition Proceedings (Mar. 2, 2001).

Schmiedl's Submission in Answer to Appeal, EP 0 504 290 Opposition Proceedings (Jun. 27, 2001).

Novis Srl's Request that Appeal be Rejected, EP 0 504 290 Opposition Proceedings (Aug 17, 2001).

Terumo's Response to Patentee's Appeal, EP 0 504 290 Opposition Proceedings (Sep. 12, 2001).

Withdrawal of Opposition by Dr. Schmiedl,, EP 0 504 290 Opposition Proceedings (Oct. 15, 2001).

Letter from Patentee Amending Main Request, EP 0 504 290 Opposition Proceedings (May 30, 2003).

Minutes of Oral Proceedings and Decision, EP 0 504 290 Opposition Proceedings (Jul. 10, 2003).

Notification of Decision and Appeal Board Decision, May 30, 2003 (Sep. 18, 2003).

Termination of the Oppositon Proceedings with the Revocation of Patent, May 30, 2003 (Sep. 23, 2003).

Medtronic's Motion for New Trial Pursuant to Fed.R.Civ.59(a), *ACS v. Medtronic Vascular, Inc.* 98–80–SLR (D. Del.) (Apr. 18, 2005).

ACS's Response to Medtronic's Motion for New Trial Pursuant to Fed. R. Civ. P. 59(a), *ACS v. Medtronic Vascular, Inc.*, 98–80–SLR (D. Del.) (Jun. 17, 2005).

Medtronic's Reply Brief in support of its Motion for New Trial Pursuant to Fed.R.Civ.P.59(a), 98–80–SLR (D. Del.) (Jul. 18, 2005).

Request of Inter Partes Reexamination of U.S. Patent No. 6,432,133 dated Mar. 30, 2007 and Exhibits 1–24.

Order Granting/Denying Request for Inter Partes Reexamination dated Apr. 24, 2007.

*Advanced Cardiovascular Systems, Inc. and Guidant Sales Corporation v. Medtronic Vascular, Inc. and Medtronic USA, Inc.*, CA No. 98–80 (SLR) ACS's Response to Medtronic's Supplemental Submission (Jan. 4, 2007).

*Advanced Cardiovascular Systems, Inc. and Guidant Sales Corporation v. Scimed Life Systems, Inc. and Boston Scientific Corporation*, CA No. IP 98–1108–C–H/G, Deposition of Lilip Lau (vol. 1), Jun. 10, 1999 (pp. 1–250).

*Advanced Cardiovascular Systems, Inc. and Guidant Sales Corporation v. Scimed Life Systems, Inc. and Boston Scientific Corporation*, CA No. IP 98–1108–C–H/G, Deposition of Lilip Lau (vol. II), Jun. 11, 1999 (pp. 252–408).

*Advanced Cardiovascular Systems, Inc. v. Scimed Life Systems, Inc.*, CA No. IP 98–1108–C–H/G, Deposition of David J. Duquette (vol. 1), Dec. 10, 1999 (pp. 1–276).

Toshiyuki Irie et al., "Relocatable Gianturco Expandable Metallic Stents", 178 Radiology 575, Feb. 1991.

Trial Transcript (Liability), vol. A, *ACS v. AVE*, 98–80–SLR (D. Del.) (Feb. 7, 2005).

Shigeru Furui et al., Hepatic Inferior Vena Cava Obstruction: Treatment of Two Types with Gianturco Expandable Metallic Stents, Radiology, Sep. 1990, 665–670, 176, Radiological Society of North America, Inc., Oak Brook, IL.

David Mirich et al., Percutaneously Placed Endovascular Grafts for Aortic Aneurysms: Feasibility Study, Radiology, Mar. 1989, 1033–1037, 170, Radiological Society of North America, Inc., Oak Brook, IL.

Michael S. Trent et al., A Balloon–Expandable Intravascular Stent for Obliterating Experimental Aortic Dissection, J. Vascular Surgery, May 1990, 707–717, 11, Elsevier.

Michael J. Wallace et al., Tracheobronchial Tree: Expandable Metallic Stents Used in Experimental and Clinical Applications, Radiology, Feb. 1986, 309–312, 158, Radiological Society of North America, Inc., Oak Brook, IL.

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 5 are determined to be patentable as amended.

Claims 2–4, 6, 7 and 8, dependent on an amended claim, are determined to be patentable.

1. A longitudinally flexible stent for implanting in a body lumen, comprising:
   a first cylindrically shaped element, a second cylindrically shaped element, a third cylindrically shaped element, up to an Nth cylindrically shaped element, the cylindrically shaped elements being generally independently expandable in the radial direction and generally aligned on a common longitudinal axis;
   other than the first and the Nth cylindrically shaped elements, each of the cylindrically shaped elements has two adjacent cylindrically shaped elements spaced in opposite axial directions;
   each of the cylindrically shaped elements having an undulating pattern of peaks and valleys, the undulating pattern of each of the cylindrically shape elements being out of phase with the undulating pattern of each of the adjacent cylindrically shaped elements; [and]
   each of the cylindrically shaped elements being interconnected to one of the adjacent cylindrically shaped elements so that the cylindrically shaped elements form a longitudinally flexible stent;
   *wherein each of the cylindrically shaped elements is not a stent; and*
   *wherein no portion of the stent overlaps with any other portion of the stent so that there are no double thickness portions.*

5. A longitudinally flexible stent for implanting in a body lumen, comprising:
   a first cylindrically shaped element, a second cylindrically shaped element, a third cylindrically shaped element, up to an Nth cylindrically shaped element, the cylindrically shaped elements being generally independently expandable in the radial direction and generally aligned on a common longitudinal axis;
   each of the cylindrically shaped elements having an undulating pattern of peaks and valleys, the undulating pattern of each of the cylindrically shaped elements being out of phase with the undulating pattern of each of the adjacent cylindrically shaped elements; [and]
   each of the cylindrically shaped elements being intereconnected to one of the adjacent cylindrically shaped elements so that the cylindrically shaped elements form a longitudinally flexible stent;
   *wherein each of the cylindrically shaped elements is not a stent; and*
   *wherein no portion of the stent overlaps with any other portion of the stent so that there are no double thickness portions.*

\* \* \* \* \*